US006183973B1

(12) United States Patent
Wright et al.

(10) Patent No.: US 6,183,973 B1
(45) Date of Patent: Feb. 6, 2001

(54) *VIBRIO VULNIFICUS* MOLECULAR PROBES, ANTIBODIES, AND PROTEINS

(75) Inventors: Anita C. Wright, Woodstock; Jan L. Powell; J. Glenn Morris, Jr., both of Baltimore, all of MD (US)

(73) Assignee: UMBI - University of Maryland Biotechnology Institute, Baltimore, MD (US)

( * ) Notice: Under 35 U.S.C. 154(b), the term of this patent shall be extended for 0 days.

(21) Appl. No.: 09/205,283

(22) Filed: Dec. 4, 1998

Related U.S. Application Data

(63) Continuation-in-part of application No. PCT/US98/01467, filed on Jun. 19, 1998.

(60) Provisional application No. 60/050,243, filed on Jun. 19, 1997.

(51) Int. Cl.[7] .......................... G01N 33/53; C12P 19/34; C12Q 1/68; C07H 21/04; C07H 21/02

(52) U.S. Cl. ............................ 435/7.2; 435/91.2; 435/6; 435/91.1; 536/23.7; 536/24.32; 536/24.33; 536/23.1

(58) Field of Search ............................ 435/6, 91.1, 91.2, 435/975, 7.2, 7.32, 7.33, 7.34, 7.35, 7.36, 7.37; 536/23.1, 24.3, 24.33, 25.3, 23.7, 24.32; 436/94

(56) References Cited

U.S. PATENT DOCUMENTS

| | | | | |
|---|---|---|---|---|
| 5,258,284 | * | 11/1993 | Morris, Jr. et al. | 435/6 |
| 5,426,025 | * | 6/1995 | Reeves et al. | 435/6 |
| 5,607,835 | * | 3/1997 | Reeves et al. | 435/6 |

OTHER PUBLICATIONS

Arias et al. Nested PCT Method for Rapid and Sensitive Detection of *Vibrio vulnificus* in Fish, Sediments and Water. Applied and Environmental Microbiology, 1965, vol. 61, No. 9. pp. 3476–3478.

Powell et al. Release of Tumor Necrosis Factor Alpha in Response to *Vibrio vulnificus* capsular Polysaccharides in In Vivo and In Vitro Models. Infection and Immunity, 1997, vol. 65, No. 9, pp. 3713–3718.

Bluyssen et al., The interferon–stimulated gene 54K promoter contains two adjacent functional interferon–stimulated response elements of different strength, which act synergistically for maximal interferon–αinducibility. Eur. J. Biochem. 220,395–402, 1994.*

* cited by examiner

*Primary Examiner*—W. Gary Jones
*Assistant Examiner*—Frank Lu
(74) *Attorney, Agent, or Firm*—Blank Rome Comisky & McCauley LLP

(57) ABSTRACT

The present invention is directed to oligonucleotides used as amplification primers and assay probes for specific and sensitive for virulent strains of *V. vulnificus*. The target sequence of the probes and primers according to present invention is a capsular polysaccharide (CPS) transport gene (wza) of *V. vulnificus*. These probes can detect wza DNA or RNA in an unknown sample suspected to have pathogenic strains of *V. vulnificus* including human, animal, or environmental samples. The invention is also directed to in vitro-expressed protein from the cloned wza for production of polyclonal or monoclonal antibody that is specific for the wza gene product and will detect the *V. vulnificus Wza* protein in a sample comprising unknown protein.

12 Claims, 11 Drawing Sheets

```
1    GTGTACAGCC GCCTGTGGAT CCCGCATACG CGGGAATGAC AGTTGGGGGC
51   GTGGCGGCGG TGTGCTGAGT TTTTTGTTCT TTGCCGCTGA ACTTAGCTCT
101  GCTTTTTCTT TTCTTATTTT TGTCATCCTC GCGAACGCGG GGAACCATCC
151  GTCAGCACCC GCCATCACTA ACTTTGAACA CAACAATCCC AGCAACTTAC
201  GTTCACTTTC CCTAAAAACA AAAAAGCCAA CACTCTTTCA AGTGTTGGCT
251  TAGAGACTAA AGCACTAAAA CTTAGTTAGT ACCAGTAGTA CCAGTAGTAC
301  CAGTAGTGTT GTTTGAAGAA ACAACAACTG CTGTTGCCGC TACTGCTGCA
351  CCTGCCGCTA CTGCTGCAGT TGTTGCTGCA CCCGCGCTAG CTGCACCTGC
401  GCCAGCACCT GCTGCTGCGC CTGTAGAAGC AGTTGTACTA GTTGCTGTAG
451  TTGCTGTTGC AGCTTCACCC GCAGCAAATG CAGTAGAAGA TACACCTAGT
501  GCAATCAACG CTGCTAATGC GATTTTTTTC ATGATTATTC CTTTGTATAT
551  ATACGTTTTC AAACATCGAT GTCGGAACTT TAATAGCTCC GGTGTTTATT
601  TTAGGTAGAA TTTGGGCGGA ATGTAAACAA TTAGTTGTAG CTGCAGCGAT
651  GTGAATTTAT GGTTTTTATC TCATTGATAG TACCGTTTGC TTAGCAAAAA
701  CAATTGTGCT CTAAGCCACA ATATGGATAA TATCCGCCCA TGATTAATAT
751  TAATAATGAC ACAATACTCA GTGTGTCATA AAACGTCAGT ACTTTGTTGC
801  AGCAAGCCAT TAGAGCTATT GCGCAGCAAA TTGTCCCAGC GCTATGTGGT
851  TTTGCGTGCT TACCAAAGGG CGGTAGCGTG TCAAAAAAGC CACAAATATG
901  GGTGGAAAAC CACACTTTTA ACGGGTTCTT ACATTTTCTT ACGTTCAGTT
951  AGCGTAGAAT GTTGTGCGAA GCTGCTTAAA ATCGCAGTCA GTGTGGGAGC
1001 TAGGCTATAA AGTATAGTTA AATGCGGTTA AGGAAAACGC CTTTAACTAT
1051 GTTGAATACC TATGCTTTCA AAAGCGTTAG AAAGAAATGG TGTTCAATCG
1101 AACCTTTGCT CATTCAAGAG TGCCGTAAAC ACTCTTAATT TAGACGATTT
```

FIG. 1A

1151 GGCTTACATG GAACTAAAAA CAAAACTTCT GCTAGCGATG CTAGCGCCTG
1201 CCTTGCTTGC CGGTTGTACT GTACCCGGCT CACATCTATC CATCGATAAT
1251 AAAAACCTTG TTGAAGTGAA CGATAGTAGC CAAGAAAGTA ACCTTTCTGA
1301 GGTGGTTAAT CTGTATCCGC TAAACGCTCA ATCGGTCACG GAATACGCCA
1351 AAGCGCAGCA TTTTGCTTCT CGCGCAAACC CAGAACTTGA TCTGCAGATC
1401 GCCCGTTATG AATACAAAGT GGGCCCTGGC GACATTCTTA ACGTTACCAT
1451 TTGGGATCAC CCTGAGTTGA CGATTCCAGC AGGCTCTTAC CGTAGTGCAT
1501 CCGAAGTAGG TAACTGGGTG CATGCAGATG GCACCATTTT CTACCCTTAC
1551 ATTGGCACTG TAGAAGTGGC AGATAAAACA GTGCGTGAGA TCCGCGCCGA
1601 TATTGCCAAA CGTCTTGCGA AGTTTATTGA AAGCCCACAG GTCGATGTCA
1651 ACGTAGCCGC GTTCCGCTCT AAGAAAGCTT ACATTACCGG TGAAGTTGAA
1701 AAACCAGGCC AACAAGCCAT CACCAATATC CCTTTAACCA TTCTGGATGC
1751 TGTAAACCGT GCTGGTGGTC TAGCGGAAGA TGCCGATTGG CGCAACGTGA
1801 CGCTTACTCG CAATGGTGAA GAGCAAGCCA TTTCTCTTTA CGCGCTTATG
1851 CAGCGTGGTG ATTTAACGCA AAACCGTTTA TTAGAGCCGG GCGATATCAT
1901 CCACGTGCCA CGCAACGACA GCCAAAAAGT GTTTGTAATG GGCGAAGTAA
1951 AAGATCCCAA ACTGCTTAAA ATGGATCGCT CTGGCATGAG CCTGACGGAA
2001 GCCCTCAGCA GCGTTGGGGG AATCAACGAG CTCTCTGCCG ATGCAACGGG
2051 CGTGTTCGTT ATCCGTACGT CAGACAACAA ATCTGAACGC ATGGCGGATA
2101 TCTACCAGCT CAACATTAAA GATGCCTCTG CACTAGTGAT TGGCACAGAA
2151 TTCGATCTAA AACCATACGA TATCGTCTAT GTGACCGCCG CACCTATTAC
2201 TCGATGGAAT CGTGTGATCA GTCAGTTAAT GCCAACGATT TATGGCTTTA
2251 ATGAACTAAC TGAAGGTGCT CTACGCGTTA AAACGTGGCC GTAAGATGAT

FIG. 1B

```
2301 TTAAAAGCGG TCCTATGGCC CTTGGGTCCT AGGGGCTAAT GGATTGGATA
2351 AGTCTCGTGT AAGCAAGGAT GGCTGATGAG GGTTTTGGGA TTTGAAAGGC
2401 TTGAAGTATG GAAAAAGAGT TCAAGACTTT CTGTTGATAT CGTCAAAGCC
2451 CTTCATCGCT GTAAAAACTA TGCATTGGTT GATCAGATAA CGCGAAGTT
```

FIG. 1C

```
  1 MLSKALERNG VQSNLCSFKS AVNTLNLDDL AYMELKTKLL LAMLAPALLA
 51 GCTVPGSHLS IDNKNLVEVN DSSQESNLSE VVNLYPLNAQ SVTEYAKAQH
101 FASRANPELD LQIARYEYKV GPGDILNVTI WDHPELTIPA GSYRSASEVG
151 NWVHADGTIF YPYIGTVEVA DKTVREIRAD IAKRLAKFIE SPQVDVNVAA
201 FRSKKAYITG EVEKPGQQAI TNIPLTILDA VNRAGGLAED ADWRNVTLTR
251 NGEEQAISLY ALMQRGDLTQ NRLLEPGDII HVPRNDSQKV FVMGEVKDPK
301 LLKMDRSGMS LTEALSSVGG INELSADATG VFVIRTSDNK SERMADIYQL
351 NIKDASALVI GTEFDLKPYD IVYVTAAPIT RWNRVISQLM PTIYGFNELT
401 EGALRVKTWP
```

FIG. 2

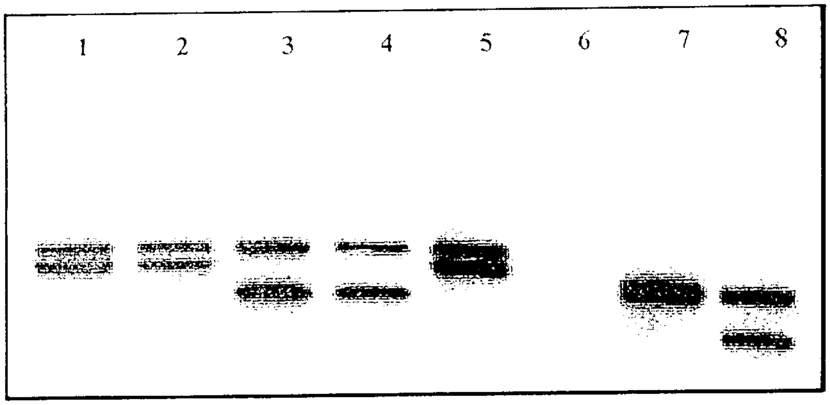

FIG. 4

```
                                          **      ***-35
TGGTTTTTATCTCATTGATAGTACCGTTTGCTTAGCAAAAACAATTGTGCTCTAAGCCAC

      **-10*       *
AATATGGATAATATCCGCCCATGATTAATATTAATAATGACACAATACTCAGTGTGTCAT
                                    ORF1:  M  T  Q  Y  S  V  C  H

AAAACGTCAGTACTTTGTTGCAGCAAGCCATTAGAGCTATTGCGCAGCAAATTGTCCCAG
K  T  S  V  L  C  C  S  K  P  L  E  L  L  R  S  K  L  S  Q
                                       ops
CGCTATGTGGTTTTGCGTGCTTACCAAAGGGCGGTAGCGTGTCAAAAAAGCCACAAATAT
R  Y  V  V  L  R  A  Y  Q  R  A  V  A  C  Q  K  S  H  K  Y

GGGTGGAAAACCACACTTTTAACGGGTTCTTACATTTTCTTACGTTCAGTTAGCGTAGAA
G  W  K  T  T  L  L  T  G  S  Y  I  F  L  R  S  V  S  V  E

TGTTGTGCGAAGCTGCTTAAAATCGCAGTCAGTGTGGGAGCTAGGCTATAAAGTATAGTT
C  C  A  K  L  L  K  I  A  V  S  V  G  A  R  L

AAATGCGGTTAAGGAAAACGCCTTTAACTATGTTGAATACCTATGCTTTCAAAAGCGTTA
                                  Wza (ORF2)     M  L  S  K  A  L

GAAAGAAATGGTGTTCAATCGAACCTTTGCTCATTCAAGAGTGCCGTAAACACTCTTAAT
E  R  N  G  V  Q  S  N  L  C  S  F  K  S  A  V  N  T  L  N

TTAGACGATTTGGCTTACATGGAACTAAAAACAAAACTTCTGCTAGCGATGCTACGGCCT
L  D  D  L  A  Y  M  E  L  K  T  K  L  L  L  A  M  L  A  P
```

FIG. 3

712A REVERSE (5' ATT CCG TGA CCG ATT GAG CGT)

712C FORWARD (5' TGC AGC AAG CCA TTA GAG CT)

712K FORWARD (5' CCA GCA ACT TAC GTT CAC TT)

752J REVERSE (5' TCG CGT TAT CTG ATC AAC CA)

FIG. 5

```
      GTACAGCCGCCTGTGGATCCCGCATACGCGGGAATGACAGTTGGGGGCGTGGCGGCGGTG
   3  ------+---------+---------+---------+---------+---------+--  62
      CATGTCGGCGGACACCTAGGGCGTATGCGCCCTTACTGTCAACCCCCGCACCGCCGCCAC

   a   V  Q  P  P  V  D  P  A  Y  A  G  M  T  V  G  G  V  A  A  V  -

      TGCTGAGTTTTTTGTTCTTTGCCGCTGAACTTAGCTCTGCTTTTTCTTTTCTTATTTTTG
  63  ------+---------+---------+---------+---------+---------+-- 122
      ACGACTCAAAAAACAAGAAACGGCGACTTGAATCGAGACGAAAAAGAAAAGAATAAAAAC

   a   C  *  V  F  C  S  L  P  L  N  L  A  L  L  F  L  F  L  F  L  -

      TCATCCTCGCGAACGCGGGGAACCATCCGTCAGCACCCGCCATCACTAACTTTGAACACA
 123  ------+---------+---------+---------+---------+---------+-- 182
      AGTAGGAGCGCTTGCGCCCCTTGGTAGGCAGTCGTGGGCGGTAGTGATTGAAACTTGTGT

   a   S  S  S  R  T  R  G  T  I  R  Q  H  P  P  S  L  T  L  N  T  -

      ACAATCCCAGCAACTTACGTTCACTTTCCCTAAAAACAAAAAAGCCAACACTCTTTCAAG
 183  ------+---------+---------+---------+---------+---------+-- 242
      TGTTAGGGTCGTTGAATGCAAGTGAAAGGGATTTTTGTTTTTTCGGTTGTGAGAAAGTTC
```

```
a    T  I  P  A  T  Y  V  H  F  P  *  K  Q  K  S  Q  H  S  F  K   -

     TGTTGGCTTAGAGACTAAAGCACTAAAACTTAGTTAGTACCAGTAGTACCAGTAGTACCA
243  -------+---------+---------+---------+---------+---------+--  302
     ACAACCGAATTTCTGATTTCGTGATTTTGAATCAATCATGGTCATCATGGTCATCATGGT

a    C  W  L  K  D  *  S  T  K  T  *  L  V  P  V  V  P  V  V  P   -

     GTAGTGTTGTTTGAAGAAACAACAACTGCTGTTGCCGCTACTGCTGCACCTGCCGCTACT
303  -------+---------+---------+---------+---------+---------+--  362
     CATCACAACAAACTTCTTTGTTGTTGACGACAACGGCGATGACGACGTGGACGGCGATGA

a    V  V  L  F  E  E  T  T  T  A  V  A  A  T  A  A  P  A  A  T   -

     GCTGCAGTTGTTGCTGCACCCGCGCTAGCTGCACCTGCGCCAGCACCTGCTGCTGCGCCT
363  -------+---------+---------+---------+---------+---------+--  422
     CGACGTCAACAACGACGTGGGCGCGATCGACGTGGACGCGGTCGTGGACGACGACGCGGA

a    A  A  V  V  A  A  P  A  L  A  A  P  A  P  A  P  A  A  A  P   -

     GTAGAAGCAGTTGTACTAGTTGCTGTAGTTGCTGTTGCAGCTTCACCCGCAGCAAATGCA
423  -------+---------+---------+---------+---------+---------+--  482
     CATCTTCGTCAACATGATCAACGACATCAACGACAACGTCGAAGTGGGCGTCGTTTACGT

a    V  E  A  V  V  L  V  A  V  V  A  V  A  A  S  P  A  A  N  A   -

     GTAGAAGATACACCTAGTGCAATCAACGCTGCTAATGCGATTTTTTTCATGATTATTCCT
483  -------+---------+---------+---------+---------+---------+--  542
     CATCTTCTATGTGGATCACGTTAGTTGCGACGATTACGCTAAAAAAAGTACTAATAAGGA

a    V  E  D  T  P  S  A  I  N  A  A  N  A  I  F  F  M  I  I  P   -

     TTGTATATATACGTTTTCAAACATCGATGTCGGAACTTTAATAGCTCCGGTGTTTATTTT
543  -------+---------+---------+---------+---------+---------+--  602
     AACATATATATGCAAAAGTTTGTAGCTACAGCCTTGAAATTATCGAGGCCACAAATAAAA

a    L  Y  I  Y  V  F  K  H  R  C  R  N  F  N  S  S  G  V  Y  F   -

     AGGTAGAATTTGGGCGGAATGTAAACAATTAGTTGTAGCTGCAGCGATGTGAATTTATGG
603  -------+---------+---------+---------+---------+---------+--  662
     TCCATCTTAAACCCGCCTTACATTTGTTAATCAACATCGACGTCGCTACACTTAAATACC

a    R  *  N  L  G  G  M  *  T  I  S  C  S  C  S  D  V  N  L  W   -
```

FIG. 6B

```
     TTTTTATCTCATTGATAGTACCGTTTGCTTAGCAAAAACAATTGTGCTCTAAGCCACAAT
 663 -------+---------+---------+---------+---------+---------+-- 722
     AAAAATAGAGTAACTATCATGGCAAACGAATCGTTTTTGTTAACACGAGATTCGGTGTTA

a    F  L  S  H  *  *  Y  R  L  L  S  K  N  N  C  A  L  S  H  N  -

     ATGGATAATATCCGCCCATGATTAATATTAATAATGACACAATACTCAGTGTGTCATAAA
 723 -------+---------+---------+---------+---------+---------+-- 782
     TACCTATTATAGGCGGGTACTAATTATAATTATTACTGTGTTATGAGTCACACAGTATTT

a    M  D  N  I  R  P  *  L  I  L  I  M  T  Q  Y  S  V  C  H  K  -

     ACGTCAGTACTTTGTTGCAGCAAGCCATTAGAGCTATTGCGCAGCAAATTGTCCCAGCGC
 783 -------+---------+---------+---------+---------+---------+-- 842
     TGCAGTCATGAAACAACGTCGTTCGGTAATCTCGATAACGCGTCGTTTAACAGGGTCGCG

a    T  S  V  L  C  C  S  K  P  L  E  L  L  R  S  K  L  S  Q  R  -

     TATGTGGTTTTGCGTGCTTACCAAAGGGCGGTAGCGTGTCAAAAAAGCCACAAATATGGG
 843 -------+---------+---------+---------+---------+---------+-- 902
     ATACACCAAAACGCACGAATGGTTTCCCGCCATCGCACAGTTTTTTCGGTGTTTATACCC

a    Y  V  V  L  R  A  Y  Q  R  A  V  A  C  Q  K  S  H  K  Y  G  -

     TGGAAAACCACACTTTTAACGGGTTCTTACATTTTCTTACGTTCAGTTAGCGTAGAATGT
 903 -------+---------+---------+---------+---------+---------+-- 962
     ACCTTTTGGTGTGAAAATTGCCCAAGAATGTAAAAGAATGCAAGTCAATCGCATCTTACA

a    W  K  T  T  L  L  T  G  S  Y  I  F  L  R  S  V  S  V  E  C  -

     TGTGCGAAGCTGCTTAAAATCGCAGTCAGTGTGGGAGCTAGGCTATAAAGTATAGTTAAA
 963 -------+---------+---------+---------+---------+---------+-- 1022
     ACACGCTTCGACGAATTTTAGCGTCAGTCACACCCTCGATCCGATATTTCATATCAATTT

a    C  A  K  L  L  K  I  A  V  S  V  G  A  R  L  *  S  I  V  K  -

     TGCGGTTAAGGAAAACGCCTTTAACTATGTTGAATACCTATGCTTTCAAAAGCGTTAGAA
1023 -------+---------+---------+---------+---------+---------+-- 1082
     ACGCCAATTCCTTTTGCGGAAATTGATACAACTTATGGATACGAAAGTTTTCGCAATCTT

a    C  G  *  G  K  R  L  *  L  C  *  I  P  M  L  S  K  A  L  E  -
```

FIG. 6C

```
     AGAAATGGTGTTCAATCGAACCTTTGCTCATTCAAGAGTGCCGTAAACACTCTTAATTTA
1083 -------+---------+---------+---------+---------+---------+-- 1142
     TCTTTACCACAAGTTAGCTTGGAAACGAGTAAGTTCTCACGGCATTTGTGAGAATTAAAT

a    R  N  G  V  Q  S  N  L  C  S  F  K  S  A  V  N  T  L  N  L  -

     GACGATTTGGCTTACATGGAACTAAAAACAAAACTTCTGCTAGCGATGCTAGCGCCTGCC
1143 -------+---------+---------+---------+---------+---------+-- 1202
     CTGCTAAACCGAATGTACCTTGATTTTTGTTTTGAAGACGATCGCTACGATGCCGGACGG

a    D  D  L  A  Y  M  E  L  K  T  K  L  L  L  A  M  L  A  P  A  -

     TTGCTTGCCGGTTGTACTGTACCCGGCTCACATCTATCCATCGATAATAAAAACCTTGTT
1203 -------+---------+---------+---------+---------+---------+-- 1262
     AACGAACGGCCAACATGACATGGGCCGAGTGTAGATAGGTAGCTATTATTTTTGGAACAA

a    L  L  A  G  C  T  V  P  G  S  H  L  S  I  D  N  K  N  L  V  -

     GAAGTGAACGATAGCAGCCAAGAAAGTAACCTTTCTGAGGTGGTTAATCTGTATCCGCTA
1263 -------+---------+---------+---------+---------+---------+-- 1322
     CTTCCATTGCTATCATCGGTTCTTTCATTGGAAAGACTCCACCAATTAGACATAGGCGAT

a    E  V  N  D  S  S  Q  E  S  N  L  S  E  V  V  N  L  Y  P  L  -

     AACGCTCAATCGGTCACGGAATACGCCAAAGCGCAGCATTTTGCTTCTCGCGCAAACCCA
1323 -------+---------+---------+---------+---------+---------+-- 1382
     TTGCGAGTTAGCCAGTGCCTTATGCGGTTTCGCGTCGTAAAACGAAGAGCGCGTTTGGGT

a    N  A  Q  S  V  T  E  Y  A  K  A  Q  H  F  A  S  R  A  N  P  -

     GAACTTGATCTGCAGATCGCCCGTTATGAATACAAAGTGGGCCCTGGCGACATTCTTAAC
1383 -------+---------+---------+---------+---------+---------+-- 1442
     CTTGAACTAGACGTCTAGCGGGCAATACTTATGTTTCACCCGGGACCGCTGTAAGAATTG

a    E  L  D  L  Q  I  A  R  Y  E  Y  K  V  G  P  G  D  I  L  N  -

     GTTACCATTTGGGATCACCCTGAGTTGACGATTCCAGCAGGCTCTTACCGTAGTGCATCC
1443 -------+---------+---------+---------+---------+---------+-- 1502
     CAATGGTAAACCCTAGTGGGACTCAACTGCTAAGGTCGTCCGAGAATGGCTTCACGTAGG

a    V  T  I  W  D  H  P  E  L  T  I  P  A  G  S  Y  R  S  A  S  -
```

FIG. 6D

```
     GAAGTAGGTAACTGGGTGCATGCAGATGGCACCATTTTCTACCCTTACATTGGCACTGTA
1503 -------+---------+---------+---------+---------+---------+-- 1562
     CTTCATCCATTGACCCACGTACGTCTACCGTGGTAAAAGATGGGAATGTAACCGTGACAT

a    E  V  G  N  W  V  H  A  D  G  T  I  F  Y  P  Y  I  G  T  V  -

     GAAGTGGCAGATAAAACAGTGCGTGAGATCCGCGCCGATATTGCCAAACGTCTTGCGAAG
1563 -------+---------+---------+---------+---------+---------+-- 1622
     CTTCACCGTCTATTTTGTCACGCACTCTAGGCGCGGCTATAACGGTTTGCAGAACGCTTC

a    E  V  A  D  K  T  V  R  E  I  R  A  D  I  A  K  R  L  A  K  -

     TTTATTGAAAGCCCACAGGTCGATGTCAACGTAGCCGCGTTCCGCTCTAAGAAAGCTTAC
1623 -------+---------+---------+---------+---------+---------+-- 1682
     AAATAACTTTCGGGTGTCCAGCTACAGTTGCATCGGCGCAAGGCGAGATTCTTTCGAATG

a    F  I  E  S  P  Q  V  D  V  N  V  A  A  F  R  S  K  K  A  Y  -

     ATTACCGGTGAAGTTGAAAAACCAGGCCAACAAGCCATCACCAATATCCCTTTAACCATT
1683 -------+---------+---------+---------+---------+---------+-- 1742
     TAATGGCCACTTCAACTTTTTGGTCCGGTTGTTCGGTAGTGGTTATAGGGAAATTGGTAA

a    I  T  G  E  V  E  K  P  G  Q  Q  A  I  T  N  I  P  L  T  I  -

     CTGGATGCTGTAAACCGTGCTGGTGGTCTAGCGGAAGATGCCGATTGGCGCAACGTGACG
1743 -------+---------+---------+---------+---------+---------+-- 1802
     GACCTACGACATTTGGCACGACCACCAGATCGCCTTCTACGGCTAACCGCGTTGCACTGC

a    L  D  A  V  N  R  A  G  G  L  A  E  D  A  D  W  R  N  V  T  -

     CTTACTCGCAATGGTGAAGAGCAAGCCATTTCTCTTTACGCGCTTATGCAGCGTGGTGAT
1803 -------+---------+---------+---------+---------+---------+-- 1862
     GAATGAGCGTTACCACTTCTCGTTCGGTAAAGAGAAATGCGCGAATACGTCGCACCACTA

a    L  T  R  N  G  E  E  Q  A  I  S  L  Y  A  L  M  Q  R  G  D  -

     TTAACGCAAAACCGTTTATTAGAGCCGGGCGATATCATCCACGTGCCACGCAACGACAGC
1863 -------+---------+---------+---------+---------+---------+-- 1922
     AATTGCGTTTTGGCAAATAATCTCGGCCCGCTATAGTAGGTGCACGGTGCGTTGCTGTCG

a    L  T  Q  N  R  L  L  E  P  G  D  I  I  H  V  P  R  N  D  S  -
```

FIG. 6E

```
     CAAAAAGTGTTTGTAATGGGCGAAGTAAAAGATCCCAAACTGCTTAAAATGGATCGCTCT
1923 -------+---------+---------+---------+---------+---------+-- 1982
     GTTTTTCACAAACATTACCCGCTTCATTTTCTAGGGTTTGACGAATTTTACCTAGCGAGA

a    Q  K  V  F  V  M  G  E  V  K  D  P  K  L  L  K  M  D  R  S  -

     GGCATGAGCCTGACGGAAGCCCTCAGCAGCGTTGGGGGAATCAACGAGCTCTCTGCCGAT
1983 -------+---------+---------+---------+---------+---------+-- 2042
     CCGTACTCGGACTGCCTTCGGGAGTCGTCGCAACCCCCTTAGTTGCTCGAGAGACGGCTA

a    G  M  S  L  T  E  A  L  S  S  V  G  G  I  N  E  L  S  A  D  -

     GCAACGGGCGTGTTCGTTATCCGTACGTCAGACAACAAATCTGAACGCATGGCGGATATC
2043 -------+---------+---------+---------+---------+---------+-- 2102
     CGTTGCCCGCACAAGCAATAGGCATGCAGTCTGTTGTTTAGACTTGCGTACCGCCTATAG

a    A  T  G  V  F  V  I  R  T  S  D  N  K  S  E  R  M  A  D  I  -

     TACCAGCTCAACATTAAAGATGCCTCTGCACTAGTGATTGGCACAGAATTCGATCTAAAA
2103 -------+---------+---------+---------+---------+---------+-- 2162
     ATGGTCGAGTTGTAATTTCTACGGAGACGTGATCACTAACCGTGTCTTAAGCTAGATTTT

a    Y  Q  L  N  I  K  D  A  S  A  L  V  I  G  T  E  F  D  L  K  -

     CCATACGATATCGTCTATGTGACCGCCGCACCTATTACTCGATGGAATCGTGTGATCAGT
2163 -------+---------+---------+---------+---------+---------+-- 2222
     GGTATGCTATAGCAGATACACTGGCGGCGTGGATAATGAGCTACCTTAGCACACTAGTCA

a    P  Y  D  I  V  Y  V  T  A  A  P  I  T  R  W  N  R  V  I  S  -

     CAGTTAATGCCAACGATTTATGGCTTTAATGAACTAACTGAAGGTGCTCTACGCGTTAAA
2223 -------+---------+---------+---------+---------+---------+-- 2282
     GTCAATTACGGTTGCTAAATACCGAAATTACTTGATTGACTTCCACGAGATGCGCAATTT

a    Q  L  M  P  T  I  Y  G  F  N  E  L  T  E  G  A  L  R  V  K  -

     ACGTGGCCGTAAGATGATTTAAAAGCGGTCCTATGGCCCTTGGGTCCTAGGGGCTAATGG
2283 -------+---------+---------+---------+---------+---------+-- 2342
     TGCACCGGCATTCTACTAAATTTTCGCCAGGATACCGGGAACCCAGGATCCCCGATTACC

a    T  W  P  *  D  D  L  K  A  V  L  W  P  L  G  P  R  G  *  W  -
```

FIG. 6F

```
     ATTGGATAAGTCTCGTGTAAGCAAGGATGGCTGATGAGGGTTTTGGGATTTGAAAGGCTT
2343 ---------+---------+---------+---------+---------+---------+ 2402
     TAACCTATTCAGAGCACATTCGTTCCTACCGACTACTCCCAAAACCCTAAACTTTCCGAA

a    I  G  *  V  S  C  K  Q  G  W  L  M  R  V  L  G  F  E  R  L  -

     GAAGTATGGAAAAAGAGTTCAAGACTTTCTGTTGATATCGTCAAAGCCCTTCATCGCTGT
2403 ---------+---------+---------+---------+---------+---------+ 2462
     CTTCATACCTTTTTCTCAAGTTCTGAAAGACAACTATAGCAGTTTCGGGAAGTAGCGACA

a    E  V  W  F  K  S  S  R  L  S  V  D  I  V  K  A  L  H  R  C  -

     AAAAACTATGCATTGGTTGATCAGATAACGCGAAGTT
2463 ---------+---------+---------+------- 2499
     TTTTTGATACGTAACCAACTAGTCTATTGCGCTTCAA

a    K  N  Y  A  L  V  D  Q  I  T  R  S  -
```

FIG. 6G

*VIBRIO VULNIFICUS* MOLECULAR PROBES, ANTIBODIES, AND PROTEINS

CROSS-REFERENCE TO RELATED APPLICATION

This is a continuation-in-part of PCT/US98/01467 filed Jun. 19, 1998 which is a continuation-in-part of U.S. Provisional Application Serial No. 60/050,243 filed on Jun. 19, 1997, the contents of which are incorporated herein by reference.

FEDERAL SPONSORSHIP OF INVENTION

The U.S. Government has a paid-up license in this invention awarded under the Merit Review Program by the United States Veterans Administration.

FIELD OF THE INVENTION

The present invention relates to nucleic acid hybridization probes, as well as antibody-based probes and vaccines, specific for virulent strains of *Vibro vulnificus* and methods for employing the same.

BACKGROUND OF THE INVENTION

*Vibrio vulnificus* (*V. vulnificus*) is a bacterium in the same family as those that cause cholera. It normally lives in warm seawater and is part of a group of vibrios that are called "halophilic" because they require salt.

*V. vulnificus* can cause disease in people who eat contaminated seafood or have an open wound that is exposed to seawater. (Blake et al., Disease caused by a marine Vibrio: clinical characteristics and epidemiology, *N. Eng. J. Med.* 300:1–5 (1979) Among healthy people, ingestion of *V. vulnificus* can cause vomiting, diarrhea, abdominal pain and wound infections. It has been associated with severe wound infections or septicemia, particularly in immunocompromised individuals and in persons with chronic liver disease, where it can cause a severe life-threatening illness characterized by fever and chills, decreased blood pressure (septic shock), and blistering skin lesions. Death can occur in as little as three days after eating raw or improperly cooked fish or shellfish that are infected with *V. vulnificus*. In the United States this pathogen contributes to the majority of deaths associated with the consumption of seafood. (Rippey, Infectious diseases associated with molluscan shellfish consumption, Clin. Microbiol. Rev. 7:419–25 (1994)) *V. vulnificus* bloodstream infections are fatal about 50% of the time. Disease is highly correlated with the ingestion of raw oysters, which are frequently colonized by numbers of *V. vulnificus* exceeding $10^4$ bacteria/g wt. (Wright et al., Distribution of *Vibrio vulnificus* in the Chesapeake Bay, *Environ. Microbiol*. 62: 717–24 (1996)). One-third of persons with septicemia present with shock, and mortalities generally exceed 50%, although the mortality rate among patients who are hypotensive within 24 hours of hospital admission exceeds 90%.

To date, effective and commercially suitable assays specific for virulent strains of *V. vulnificus*, are not known in the art, and there has been a need to provide a means to detect and/or diagnose humans or animals infected with virulent strains of *V. vulnificus*. This bacterium is ubiquitous to the estuarine environment world wide, and in summer months virtually all oysters from the Atlantic and Gulf of Mexico are contaminated with this organism. Thus, there is no way to certify oysters as being pathogen-free, and the oyster industry in Southern states has suffered tremendous loses as many states will no longer accept Gulf Coast oysters. Warnings about the health risks related to *V. vulnificus* disease are now required for all oyster products in the U.S.

Traditional tests for the presence of *V. vulnificus* in food and water, as well as in patient samples (stool, blood, etc.), require the bacterium to be grown or cultured in a growth medium and examined morphologically and biochemically, a process that can take as long as one week. Such a procedure is ineffective when a patient requires a rapid diagnosis, as infection can be fatal in as little as three days. Similarly, such a process can not practically be applied to seafood safety testing which requires large shipments of seafood to be examined in a fast and inexpensive manner.

A faster way to identify the presence of these microbes is to use an antibody that recognizes and specifically binds to a specific part of the bacterium. See, for example, Tamplin, M. L. et al.: Enzyme immunoassay for identification of *Vibrio vulnificus* in seawater, sediment, and oysters, *Applied and Environmental Microbiology*, 57:1235–1240 (April 1991), which describes an enzyme immunoassay for the identification of *V. vulnificus* in seawater, sediment and oysters. Also, DNA probes for detecting this pathogen are described in U.S. Pat. No. 5,258,284 to Morris et al., and U.S. Pat. No. 5,607,835 to Reeves et al.

A key disadvantage of these known probes and antibodies is that they detect both virulent and non-virulent strains of *V. vulnificus*. The virulence of this microbe is linked to expression of capsular polysaccharide (CPS) on the surface of the bacterium. These capsules function to envelop the bacteria in a protective coating that is required for the evasion of host innate immune defenses such as phagocytosis and complement-mediated cell lysis. Hence, those bacteria that produce life-threatening systemic infections usually express CPS which can be a target for specifically detecting or attacking these harmful bacterium. Unfortunately, many pathogens can exhibit multiple types of CPS, which may confound identification and reduce or eliminate vaccine efficacy. On the other hand, CPS export systems are more highly conserved among species yet retain a high degree of species-specificity. Thus, these transport systems are potential targets for probes that are both species-specific and virulence specific.

In addition to the need for more specific diagnostics, there is also a need for improved vaccines and therapeutics for *V. vulnificus* exposure. Infection is usually treated with antibiotics such as doxycycline or cephalosporin. However, the rapid progression and high mortalities associated with this disease indicate that the current antibiotic therapies are ineffectual. A vaccine for this disease is currently not available, and reliable methods to eliminate *V. vulnificus* from oysters do not exist.

For the foregoing reasons, it would be desirable to have DNA probes and antibodies that are specific for only virulent forms of *V. vulnificus* and to develop improved vaccines and therapeutics for *V. vulnificus* exposure.

SUMMARY OF THE INVENTION

In view of the aforementioned needs, it is a key object of the present invention to provide a fast, accurate, and inexpensive assay comprising nucleic acid probes (including PCR primers) that are specific and sensitive for virulent strains of *V. vulnificus*. The target sequence of the probes and primers according to present invention is a capsular polysaccharide (CPS) transport gene (wza) of *V. vulnificus*. These probes can detect wza DNA or RNA in an unknown sample suspected to have pathogenic strains of *V. vulnificus* including human, animal, or environmental samples.

More specifically, the probe according to the present invention (a) comprises a nucleotide sequence of at least 15 bases in length, (b) specifically hybridizes under appropriate conditions to the sequence shown in FIG. 1, and (c) is labeled with a detectable marker.

Such a probe may be employed to detect the presence of pathogenic strains of *V. vulnificus* in a sample comprising an unknown nucleic acid by (1) hybridizing, under appropriate stringency conditions, the labeled nucleic acid hybridization probe with the unknown nucleic acid in the sample; and (2) assaying for cross-hybridization of the labeled nucleic acid hybridization probe with the unknown nucleic acid in the sample so as to detect the presence of virulent strains of *V. vulnificus* in the sample.

Oligonucleotides primers may be employed for amplification of *V. vulnificus* wza DNA or RNA in the polymerase chain reaction (PCR) assay. The oligonucleotide primers are designed to preferentially hybridize to what has been found to be a species-specific target of the organism's genome. Preferential hybridization means, for example, that the inventive primers amplify the target sequence in *V. vulnificus* with little or no detectable amplification of target sequences of other species of bacteria that may have homologous wza genes, such as *Escherichia coli.*

The inventive assay has distinct advantages over the routine methods used presently. This assay can be performed in several hours rather than the 4 to 7 days required of prior art assay. The inventive assay is expected to become even more rapid as DNA technology improves. The present invention also has the advantage over prior art detection systems that detect all *V. vulnificus* strains, virulent and nonvirulent, since wza expression is required for virulence and is therefore a good candidate for a virulence-specific probe for *V. vulnificus.*

Another object of the invention is to provide in vitro-expressed protein from the cloned wza for production of polyclonal or monoclonal antibody that is specific for the wza gene product and will detect the *V. vulnificus* Wza protein in a sample comprising unknown protein. In vitro derived proteins may be derived from expression of the wza gene cloned into vectors that provide a promoter for over expression of the gene product. The cloned gene product can be separated and purified and inoculated into rabbits or mice for the production of monoclonal antibody. The polyclonal or monoclonal antibody may be applied to the prevention and/or treatment of *V. vulnificus* infection in either humans or animals whereby the binding of antibody to the Wza protein blocks the transport and expression of CPS on the bacterial cell surface.

Another object of the present invention is to provide novel vaccines to prevent *V. vulnificus* infections in humans. Although Wza and other CPS export proteins retain some degree of species-specificity, they are much more highly conserved among species than are the enzymes involved in the pathway for CPS biosynthesis. This conservation provides the basis for a broad-based vaccine that will be effective against strains of multiple CPS types. The outer membrane location of the CPS transport system presents a target for vaccine development, as binding of blocking antibody may disrupt CPS expression. Outer membrane protein vaccines have been shown to be effective in vaccine trials and may be more immunogenic than CPS preparations (Herbert et al., Meningococcal vaccines for the United Kingdom, *Commun. Disease Reporter CDR Review* 5(9) R130-5 (August 1995)). Additionally, CPS transport mutants, such as the nonpolar wza mutant may provide ideal vaccine candidates for live whole cell vaccines as they have retained the intact CPS in a more immunogenic form (i.e. conjugated to lipoproteins), but they have lost virulence due to lack of surface CPS. Thus, due to lack of surface CPS, they are readily phagocytized, but should still provide ample CPS for antigen processing and maximum immune response. Thus, antibody to Wza may be employed as prophylaxis or treatment in the form of passive antibody to the outer membrane protein, or through the use of attenuated strains as live vaccine constructs. As the Wza outer membrane transport system has been identified in a number of species, this methodology may be applicable to multiple bacterial pathogens.

With the foregoing and other objects, advantages and features of the invention that will become hereinafter apparent, the nature of the invention may be more clearly understood by reference to the following detailed description of the invention, the appended claims and to the several views illustrated in the figures.

BRIEF DESCRIPTION OF THE DRAWINGS

FIG. 1 is the DNA sequence (SEQ ID NO: 1) from the *Vibrio vulnificus* CPS locus. The DNA includes all of the wza (ORF2) gene, as well as the sequence upstream of wza (including the promoter region and ORF1) and downstream of wza (including primer 752J.

FIG. 2 is the Wza deduced amino acid sequence (SEQ ID NO: 2) from wza (ORF2) gene of the Vibrio vulnificus CPS locus.

FIG. 3 is the nucleotide and deduced amino acid sequence (SEQ ID NO: 3) of the region upstream from the *V. vulnificus* wza (ORF2) gene. Both ORF1 and the begnning of ORF2 (wza gene) are shown. Promoter region (−10 and −35) preceding ORF1 is indicated and underlined. The transcriptional; antideterminator, ops, sequence is double underlined, and a potential ribosome binding site (RBS) for wza is indicated and underlined. The proposed start of translation is indicated by the arrow.

FIG. 4 is a photograph of a Southern Blot showing the translucent (nonencapsulated) variant of *V. vulnificus* lacks the wza gene. Shown are the chromosomal digests probed with the wza gene for the following strains of *V. vulnificus* MO6-24/O (M/O), MO6-24/T (M/T), E4125/O (M/O), E4125/T (E/T), 345/O (3/O), 345/T (3/T), LC4/O (L/O), LC4/T (L/T) in lanes 1–8 respectively. All strains are positive for wza except 345/T.

FIG. 5 is an exemplary group of probes and primers that can be used according to the present invention.

FIG. 6 is the complete nucleotide and deduced amino acid sequences (SEQ ID NO: 1) for the region including and surrounding the *V. vulnificus* wza gene. The location and direction of transcription for ORF1 and wza (ORF2) gene are shown above the nucleotide sequence and are indicated by large arrows. Small arrows show the location and direction of the exemplary primers and probes illustrated in FIG. 5 and the sequences are underlined.

REFERENCES

The following publications are incorporated herein by reference.

Dieffenbach, C. W. and Dveksler, G. S. 1995. PCR Primer: A Laboratory Manual. Cold Spring Harbor Laboratory Press, New York Innis, M., D. Gelfand, J. Sninsky and T. White (eds.). 1990. PCR protocols: A guide to methods and applications. Academic Press Inc., New York, N.Y.

Sambrook, G., Fartsch, E. F., Maniatis, T. 1989. *Molecular Cloning, A Laboratory Manual*, Second Edition. Cold Spring Harbor Laboratory, Cold Spring Harbor, N.Y.

Colligan, J. E., et al. (eds.). 1997. *Current Protocols in Immunology*. John Wiley & Son, Inc.

Harlow, E., Lane, D. 1988. *Antibodies, A Laboratory Manual*, Cold Spring Harbor Laboratory, Cold Spring Harbor, N.Y.

DETAILED DESCRIPTION OF THE INVENTION

Definitions

The following terms are defined herein as follows:

"DNA amplification" as used herein refers to any process which increases the number of copies of a specific DNA sequence. A variety of processes are known. One of the most commonly used is the Polymerase Chain Reaction (PCR) process of Mullis as described in U.S. Pat. Nos. 4,683,195 and 4,683,202 both issued on Jul. 28, 1987. In general, the PCR amplification process involves an enzymatic chain reaction for preparing exponential quantities of a specific nucleic acid sequence. It requires a small amount of a sequence to initiate the chain reaction and oligonucleotide primers which will hybridize to the sequence. In PCR the primers are annealed to denatured nucleic acid followed by extension with an inducing agent (enzyme) and nucleotides. This results in newly synthesized extension products. Since these newly synthesized sequences become templates for the primers, repeated cycles of denaturing, primer annealing, and extension results in exponential accumulation of the specific sequence being amplified. The extension product of the chain reaction will be a discrete nucleic acid duplex with a termini corresponding to the ends of the specific primers employed. In the present invention the amplification results in an extension product of one sequence localized between two genes. Since these genes are multiple copy and the sequence target is between each copy, there will be exponential amplification for each of the copies. The extension products sizes using discrete primers will provide a specific fingerprint for each microorganism.

"Primer" means an oligonucleotide comprised of more than three deoxyribonucleotides used in amplification. Its exact length will depend on many factors relating to the ultimate function and use of the oligonucleotide primer, including temperature, source of the primer and use of the method. The primer can occur naturally (as a purified fragment or restriction digestion) or be produced synthetically. The primer is capable of acting as an initiation point for synthesis, when placed under conditions which induce synthesis of a primer extension product complementary to a nucleic acid strand. The conditions can include the presence of nucleotides and enzymes such as DNA polymerase or TAQ polymerase at a suitable temperature and annealing and extension times as well as the appropriate buffer (pH, magnesium chloride ($MgCl_2$) and potassium chloride (KCl) concentrations, and adjuncts). In the preferred embodiment the primer is a single-stranded oligodeoxyribonucleotide of sufficient length to prime the synthesis of an extension product from a specific sequence in the presence of an inducing agent. In the present application in the preferred embodiment the oligonucleotides are usually between about 10 mer and 35 mer. In the most preferred embodiment they are between 17 and 24 mer. Sensitivity and specificity of the oligonucleotide primers are determined by the primer length and uniqueness of sequence within a given sample of a template DNA. Primers which are too short, for example, less than 10 mer may show non-specific binding to a wide variety of sequences in the genomic DNA and thus are not very helpful. Thus one primer of each pair is sufficiently complementary to hybridize with a part of the sequence in the sense strand and the other primer of each pair is sufficiently complementary to hybridize with a different part of the same repetitive sequence in the anti-sense strand.

"Nucleotide sequence" as used herein means any nucleic acid of more than 3 bases in length used to facilitate detection or identification of a target nucleic acid sequence, including both probes and primers.

"Stringent annealing conditions" means that in those conditions the specificity, efficiency and fidelity of the PCR amplification will generate one and only one amplification product that is the intended target sequence.

"Hybridize" or "Preferentially Hybridize" means the joining of two single stranded nucleotide sequences that are about 80% or more complementary.

Probes

The present invention relates to nucleic acid probes which are highly specific for virulent strains of *V vulnificus* (but not for nonvirulent strains) that bind to a portion of the wza gene of *V. vulnificus*. To create DNA or RNA probes for virulent stains of an organism one must 1) identify a genetic locus that is associated with virulence, 2) isolate and sequence the gene, 3) confirm that the gene is required for virulence, 4) demonstrate the gene function, and 5) design oligonucleotide probes or primers for PCR that are specific for the species and for strains that are virulent.

The probes are specific for a previously unknown DNA sequence for the CPS transport gene, wza shown in FIG. 1 (SEQ ID NO: 1), which it has been determined in accordance with the present invention to be required for virulence. In particular, the sequence comprises a 3.5 kb fragment of which a 1.2 kb is the wza gene (ORF2). This sequence was selected, as described below, to provide sequences having high selectivity and specificity as deoxynucleotide hybridization probes or primers for DNA amplification.

The significance of the gene as a target for diagnostic probes according to the present invention was determined as follows. The DNA from the wza gene was shown to be specific for virulent *V. vulnificus* and did not hybridize with DNA from other Vibrio or non-Vibrio species under stringent conditions. Homology of DNA sequences was demonstrated for all opaque virulent clinical and environmental isolates of *V. vulnificus* examined (n=4). On the other hand, deletion or genetic rearrangements of wza or flanking DNA were observed in 2 of 4 avirulent strains. Further, the majority (88%) of opaque, encapsulated environmental *V. vulnificus* isolates (n=97) were positive for a wza oligonucleotide probe, confirming the conservation of this transport gene. In addition, the occurrence of isolates that were negative for the wza probe was significantly higher among translucent than opaque environmental phase variants (Fisher's Exact test, 2 tail, p=0.007.), suggesting a possible deletion-mediated mechanism for loss of CPS expression and thus virulence. Similar mechanisms have been demonstrated in *Haemophilus influenzae*. These data support the application of wza nucleic acid sequences or antibody derived from the expressed gene product for development of molecular probes for the discrimination of virulent vs. avirulent strains of *V. vulnificus.*

The importance of CPS as a virulence determinant for *V. vulnificus* was confirmed by the loss of virulence phenotype in acapsular transposon mutants (Wright et al., Phenotypic evaluation of acapsular transposon mutants of *Vibrio vulnificus, Infect. Immun.* 58: 1769–73 (1990)). Encapsulated strains of *V. vulnificus* have opaque colony morphology and exhibit a reversible phase variation to translucent morphotypes with reduced or patchy expression of surface polysaccharide. The phenotype of partially encapsulated translucent phase variants is intermediate between the fully encapsulated parent strains and acapsular transposon mutants, in terms of virulence or sensitivity to phagocytosis and complement-mediated cell lysis. This correlation suggest a positive relationship between the amount of expressed CPS and virulence and is consistent with observations in *Escherichia coli* in which enhanced virulence in mice correlated with growth conditions that significantly increased CPS expression (Vermeulen et al., Quantitative relationship between capsular content and killing of K1—encapsulated *Escherichia coli, Infect Immun.* 56:2723–30 (1988)).

$LD_{50}$ determinations (Reed and Meunch, A simple method of estimating the fifty percent endpoints, *Am. J. Hyg.* 27:493–497 (1938)) in mice (n=5) agreed with previously published data (Wright et al., supra, 1990) which demonstrated that the translucent phase variant *V. vulnificus* M06-24T ($LD_{50}$=1.9×$10^7$) was less virulent than the parental, encapsulated M06-24/O ($LD_{50}$=4.0×$10^5$). Decreased virulence of CPS transport mutant M06-24/31T ($LD_{50}$=1.6×$10^7$) was observed in comparison to the opaque parent strain but was similar to that of the minimally encapsulated translucent phase variant. Acapsular mutant *V. vulnificus* CVD752 was less virulent than other strains, and no deaths were observed at the highest concentration of bacteria ($10^8$) inoculated. These data indicate that expression of wza is required for full virulence of *V. vulnificus*, and that oligonucleotide sequences derived from wza can be used to specifically detect virulent strains of *V. vulnificus*.

The CPS transport gene wza shown in FIG. 1 was cloned using conventional techniques described in the Examples below. The length of the probes are preferably at least about 15 bases in length and are labeled with a detectable marker.

Selection of expected suitable sequences to be used for nucleotide hybridization probes specific for *V. vulnificus* may be based on the presence of one or more of the following characteristics which are well known to provide some expectation of probe specificity:

(1) moderate/high guanine/cytosine (GC) ratios, (2) lack of internal repeats, (3) regions within major hydrophobic or hydrophilic segments.

Hybridization can be carried out in solution by well-known methods (see, generally, for probe design, hybridization, and stringency conditions, Ausubel et al., eds. *CURRENT PROTOCOLS IN MOLECULAR BIOLOGY*, Wiley Interscience, New York, sections 6.3 and 6.4 (1990), or on a solid support see e.g., Sambrook et al, *MOLECULAR CLONING: A LABORATORY MANUAL*, Cold Spring Harbor Laboratory, Cold Spring Harbor, N.Y. (1989) the contents of each of which are herein incorporated by reference).

Examples of probe labeling and detection include radioisotope labeling, such as end-labeling with [$y^{-32}$P] ATP using T4 polymerase kinase (See, e.g., Sambrook, supra, and Miliotis et al, Development and testing of a synthetic oligionucleotide probe, *J. Clin. Microbiol.* 27:1667–1670 (1989)), the contents of each of which are herein incorporated by reference. Other examples include non-radioisotope labeling, such as incorporation of a modified base directly linked to a detectable marker (see, e.g., Jabloaski et al., *Nucleic Acids Res* 14:6115–6128 (1986) and Olive et al, Detection of human rotavirus by using an alkaline phosphatase-conjugated synthetic DNA probe in comparison with enzyme linked immunoassay and polyacrylamide gel analysis, *J. Clin Microbiol.* 27(1):53–7(1989) the contents of each of which are herein incorporated by reference).

In the context of the present invention, "stringent" hybridization conditions refers to hybridization at a temperature of about 10°–25° C. below the melting temperature of a perfectly base-paired double stranded DNA having a base composition equal to that shown in FIG. 1 or fragments thereof. Also in the context of the present invention, "non-stringent" hybridization conditions refers to hybridization at a temperature of at least about 35° C. below the melting temperature of a perfectly base-paired double stranded DNA having a base composition equal to that of the wza gene sequence or fragments thereof.

Hybridization can be carried out, on a solid support using a variety of different procedures. The specific procedure employed is not critical to the present invention. One such procedure involves purifying the unknown DNAs or RNAs, immobilizing such on a solid support in single-stranded form, followed by hybridization with a wza specific nucleic acid probe which has been labeled with a marker (for example, as described in Sambrook, supra. Miliotis, supra, and Olive, supra.)

Hybridization in situ can be performed, for example, on glass slides and the end result of the procedure is viewed through a microscope. In this procedure, the DNA or RNA is not purified from the cells but is left with all of the other cellular components on the slide. (See e.g., Nuovo, G. J. (1994) in PCR *In-Situ Hybridization* Raven Press, New York herein incorporated by reference)

When employing wza RNA as a hybridization probe for detecting wza DNA in an unknown sample of DNA, it is preferable that the DNA-RNA hybrids be formed after first hybridizing under stringent hybridization conditions, followed by treatment with pancreatic RnaseA (about 20 ug/ml in 50 mM NaCl (pH 7.0) at room temperature (about 20°–30° C.), followed by washing under stringent hybridization conditions.

The wza specific DNA nucleic acid probes of the present invention can be labeled by well known means of both radioactive and non-radioactive markers such as biotin, an enzyme, or a fluorescent group. Biotin acts as a hapten-like group and can be bound to DNA or RNA and detected by binding an avidin-conjugated enzyme or streptavidin-conjugated enzyme to the biotin, followed by washing to remove non-specifically bound enzyme. Upon addition of appropriate substrates for the enzyme, the conversion of the substrate to a colored product can be detected. Examples of such enzymes include alkaline phosphatase and horseradish peroxidase.

In addition, fluorescent molecules, such as fluorescein and rhodamine can be chemically conjugated to avidin or streptavidin and employed as non-radioactive markers.

Alternatively, the above described enzymes or fluorescent molecules can be chemically conjugated directly to the wza encoding DNA or RNA nucleic acid probes as described in, e.g., Renz, Polynucleotide-histone H1 complexs as probes for blot hybridization *EMBO J.* 2(6):817–22 (1983), and used in this manner as hybridization probes.

The thus labelled wza nucleic acid probes can be used as described above for hybridization with an unknown sample of DNA or RNA, particularly an unknown sample comprising DNA or RNA derived from human or animal blood, to determine if the sample contains wza encoding DNA or RNA.

The probes are preferably at least 15 bases in length, and more preferably between 20 and 50 bases in length. The probes may be either sense or antisense in orientation.

In use, the probes according to the present invention are employed to detect the presence of virulent strains of *V. vulnificus* in a sample by hybridizing (a) nucleic acid probes that comprise sense and/or antisense nucleic acid sequences corresponding to a portion of the wza gene which are highly specific and sensitive for the wza gene and (b) assaying for co-hybridization between the probes and the unknown nucleic acid.

Primers

When the amount of DNA in the sample may be insufficient to provide detectable hybridization using the above-described probes, an amplification method such as PCR, LCR, NASBA®, and Strand Displacement may be employed. The oligonucleotide primers are designed to preferentially hybridize to the wza gene or a region thereof. Preferential hybridization means, for example, that the inventive primers amplify the target sequence in *V. vulnificus* with little or no detectable amplification of target sequences of other species of bacteria that may have homolgous wza genes, such as *Escherichia coli.*

Using the sequence information shown in FIG. 1, PCR primers are designed which hybridize to the wza sequence using techniques known in the art (such as those described *PCR Primer: a Laboratory Manual* (Dieffenbach et al. 1995). Depending on the particular primer sequences selected, the best PCR conditions (annealing temperatures, pH, adjuncts, extension times, cycle numbers, salt concentrations) can be determined using any of a variety of commercially available computer programs such as GENE JOCKEY™ II (Biosoft, Ferguson, Mo.), MacVector (International Biotechnologies, Inc., New Haven, Conn.) and Primer Design III (Scientific Educational Software, Durham, N.C.). Amplified products are resolved by agarose gel electrophoresis in the presence of ethidium bromide, recovered from the gel, and cloned into a commercially available cloning vector system (pGEM-T Vector, Promega, Madison, Wis.). Recombinant plasmids are transformed into competent cells and selected following the manufacture's protocol. Isolation of plasmid DNA is carried out using the method of Sambrook et al. supra (1989). For each PCR product, several clones with inserts are sequenced to confirm the sequence using an available DNA sequencing method (Applied Biosystems 373 DNA Sequencer, Perkin Elmer, Foster City, Calif.).

The criteria for selecting the region to be amplified within the target sequence are the following: length, sequence composition and melting temperature, and the ultimate applications, as will be readily known to those skilled in the art. The length of the region of the Wza that is selected to be amplified depends on the PCR primers selected. This length can be from 50 bp to full length, but is preferably from about 100 bp to 1200 bp, and optimally between about 250 and 600 bp. PCR conditions (annealing temperatures, pH, adjuncts, extension times, cycle numbers, salt concentrations) are determined following prescribed protocols in standard manuals such as *PCR Primer: a Laboratory Manual* (Dieffenbach et al. 1995). Primer lengths can be between 10 and 35 bases long, are preferably between 15 to 25 bases long, but most preferably will be between 17 and 24 bases long. Primers are tested against the target organism, related species, and the host in the case of a parasite. Sensitivity can be determined using different dilutions of target DNA for the PCR assay. General information about PCR and the design of primers not described herein may be found in Sambrook et al. (1989).

In addition to the PCR-diagnostic assay, the Wza region can be used to develop a quantitative PCR assay retaining specificity that will permit the accurate assessment of the numbers of *V. vulnificus* in tissue and hemolymph of infected oysters. For a number of applications and studies, it is essential to determine accurately the number of bacteria in different samples. Competitive PCR offers a precise method for determination of the concentration of target molecules which can than be calibrated to calculate cell number. The basis for competitive PCR is the design of a competitor template whose product can be distinguished from experimental template but at the same time is extremely similar in its composition. This competitor template is added to the PCR reaction is known quantities and co-amplified with sample DNA and the ratio of known amount of competitor product to experimental product can be used to determine the DNA concentration of the experimental template and correlate the amount of template produced with a standard cell number. Kits available on the market (PCR Mimic System, Clontech, Palo Alto, Calif.) can be used to construct competitive fragments for quantitative PCR.

In a preferred embodiment two alternative forward primers are used in the PCR amplification along with one preferred reverse primer (see FIG. 4 and Example 1 below). Additional primers, of lengths greater or less that those described here, derived from this sequence could also function in the diagnostic test for *V. vulnificus.*

A number of automated PCR amplifying means are known in the art such as thermal cyclers, robotic devices, and automatic pipette and sampling machines for removing extension products from the PCR reaction at appropriate times and transferring the sample for either chromatography, gel or capillary electrophoresis, mass spectrometry or other methods or techniques used to separate the samples.

In summary, isolated sequences of the wza gene sequence for nucleotide probes or PCR primers may be based on the following criteria:

(a) sequences corresponding to portions of sequences as shown in FIG. 1 including the open reading frame for wza gene or flanking sequences of the open reading frame that may include regulatory elements necessary for expression, (b) total nucleotide sequences of at least 15 bases in length; Examples include the sequences shown in FIG. 4.

(c) Sequences derived from commercially available computer software designed to determine oligonucleatide probes and primers for DNA hybridization or PCR. Examples include Gene Jockey (Biosoft, Ferguson Mo.), MacVector (International Biotechnologies, Inc. New Haven, Conn.), and Primer Design III (Scientific Educational Software, Durham, N.C.).

(d) Sequences determined by techniques known in the art such as those described in *PCR Primer, a Laboratory Manual* (Dieffenbach et al., 1995) which include (1) moderate/high guanine/cytosine (GC) ratios, (2) lack of internal repeats (e) Oligonucleotide sequences which hybridize with wza sequences under stringent conditions as previously described in Wright et al., Rapid identification of *Vibrio vulnificus* on nonselective media with an alkaline phosphatase labeled oligonucleotide probe, *Appl. Environ Microbiol.* 59: 541–546 (1993); and Wright et al., Distibution of *Vibrio vulnificus* in the Chesapeake Bay, *Appl. Environ Microbiol.* 62: 717–724 (1996) herein incorporated by reference. These oligonucleotide sequences are labeled with a detectable marker.

Use of Probes and Primers

In the context of testing the safety of seafood, the unknown sample comprising DNA or RNA can be derived from water, shellfish meat, shellfish culture, and the like. More specifically, water samples include salt water, fresh water, and brackish water obtained from rivers, streams lakes, marshes or other bodies of water, ground water, piped water, filtration or purification plants effluents, soil, earth, and rock. Seafood tested would most likely be shellfish including oysters, clams, mussels, crabs, lobster, crayfish, and the like.

Samples can also include those from a human source, such as a human tissue or a body fluid. Human tissues can include, e.g., blood, throat, skin, lung, organ, muscle, and bone. Body fluids can include, e.g., sputum. ear fluids, stool, urine, vaginal fluid, uterine fluid, and amniotic fluid. The unknown sample of DNA or RNA can be obtained by, for example, by taking a blood, stool or wound sample by scraping the throat or by swabbing the throat to obtain exfoliated cells and enitured to provide detectable levels of *V. vulnificus* nucleic acid. In addition, the unknown sample comprising DNA or RNA can be obtained from bacterial cells in which DNA from an animal tissue has been cloned using well known means as described, e.g. in Sambrook et al.: 1, *MOLECULAR CLONING: A LABORATORY MANUAL*, Cold Spring Harbor Laboratory, $2^{nd}$ ed., Cold Spring Harbor, N.Y. (1989).

In the methods of the present invention, assaying for cross-hybridization can be carried out by assaying for the presence of radioactive or non-radioactive marker associated with double-stranded nucleic acid hybrids. The methods for determining whether a specific marker is present will depend upon the marker employed and are well-known in the art.

According to the method of the present invention, the liquid mixture is used in the amplification cycle of the PCR method. The amplification cycle comprises steps of: (i) denaturing a double-strand DNA (for about 10 seconds to 2 minutes at about 90° C., to 95° C.) (ii) annealing the single-strand DNA with the first and second primers (for about 30 seconds to about 3 minutes at about 37° C. to 70° C., and (iii) extending a DNA by the DNA polymerase (for about 30 seconds to about 5 minutes at about 65° C. to 80° C.). In the present invention the above mentioned amplification cycle is repeated 10 to 60 times, preferably 20 to 40 times. In the final cycle it is preferable to extend the heating time of the step (iii) to about 5 to 10 minutes so as to complete the DNA synthesis.

Another important use of the present invention is a kit for detecting *V. vulnificus*. This kit preferably comprises a container having a pair of outwardly-directed PCR primers to the wza region of *V. vulnificus*. This kit can have the PCR primers provided in Example 1 or other alternatives created as described above. One skilled in the art will readily recognize that the number and type of primers which are in the kit will depend on the use of the kit as well as the sequences to be detected. The kit would also include the buffers, DNA polymerase, and dideoxinucleotides, KCl and $MgCl_2$ and all other reagents necessary to conduct PCR amplification.

Protein, Antibody, & Vaccine

The present invention also relates to in vitro-expressed protein from the cloned wza for production of polyclonal or monoclonal antibody that is specific for the wza gene product and will detect the *V. vulnificus* Wza protein in a sample comprising unknown protein.

The cloned *V. vulnificus* wza gene can be used to produce the transcribed mRNA sequence that can be translated into protein, using either expression vectors in *E. coli* or in vitro transcription/translation systems. The complete *V. vulnificus* wza gene has been cloned into pGemTEasy (Promega, Madison, Wis.) in both orientations. Thus, it may be transcribed from the either the T7 or SP6 RNA polymerase promoter flanking the multiple cloning site for in vitro transcription/translation systems such as *E. coli* T7 Extract System for Circular DNA (Promega, Madison, Wis.). Alternatively, the wza sequence could be cloned into any of a number of commercially available expression systems, such as the Xpress system (Invitrogen, Carlsbad, Calif.) or Strep-TagII (Genosys, Woodlands, Tex.). These systems permit fusion of the gene product of interest to “tags” such a histidine residues or streptavidin binding peptide that can be used to easily purify the protein fusion. The tag is later cleaved enzymatically, and removed by column chromatography.

Another object of the invention is to provide in vitro-expressed protein from the cloned wza for production of polyclonal or monoclonal antibody that is specific for the wza gene product and will detect the *V. vulnificus Wza* protein in a sample comprising unknown protein. In vitro derived proteins may be derived from expression the wza gene cloned into vectors such as pBluescript (Stratagene) that provide a promoter for over expression of the gene product. In vitro derived proteins can be derived from expression of the wza gene cloned into vectors such as the Xpress System (Invitrogen, Carlsbad, Calif.) which provide a gene fusion to a poly histidine tag that can be used to extract the fusion product on a Ni column that bind histidine. The cloned gene product can be separated and purified from the histidine tag by enzymatic digestion and a $2^{nd}$ extraction with the Ni column.

Purified wza gene product can be inoculated into rabbits for the production of polyclonal antibody or into BalbC mice for production of monoclonal antibody. The polyclonal or monoclonal antibody may also be applied to the prevention and/or treatment of *V. vulnificus* infection in either humans or animals whereby the binding of antibody to the Wza protein blocks the transport and expression of CPS on the bacterial cell surface.

Purified Wza protein derived from recombinant DNA expressed in vitro or in *E. coli*, as described above, can be used to produce polyclonal or monoclonal antibody in animals, using standard protocols known in the art such as those described in *Antibodies: A Laboratory Manual*, Cold Spring Harbor Laboratory Press, Cold Spring Harbor N.Y. (E. Harlow & D. Lane, 1988), or *Current Protocols in Immunology*. John Wiley & Son, Inc. (Colligan et al., 1991–1997) herein incorporated by reference. These antibodies can be used in antibody-based detection and/or protein purification systems for Wza from *V. vulnificus* or possible other Wza homologues that may cross-react with this antibody. Other antibody applications include immunoglobulin therapy or passive immunization for person with *V. vulnificus* disease or those at risk. Expression of CPS and Wza may also be required for survival of *V. vulnificus* in oysters; therefore, blocking antibody could function to facilitate the removal of *V. vulnificus* from oysters and presents a potential candidate for a method of decontaminating oysters.

A vaccine for this disease is currently not available, and reliable methods to eliminate *V. vulnificus* from oysters do not exist. The outer membrane location of the wza gene product supports its use as a protective antigen. Thus, antibody may block expression of CPS and prevent dissemination of the bacteria in the host. The advantages of Wza as an immunogen over the CPS are the conservation of Wza sequences among virulent strains in comparison to the multiple CPS types (Bush et al., Classification of *Vibrio vulnificus* strains by the carbohydrate composition of their capsular polysaccarides, *Anal. Biochem.* 250:186–195 1997), as well as the increased immunogenicity of outer membrane proteins over CPS. In addition the Wza mutants that are able to produce CPS but do not express it on the surface offer the potential for an attenuated live vaccine strain, as it should be readily eliminated by the host but will still present the CPS antigen to the immune system.

In Gram-negative bacteria, CPS is synthesized in the cytoplasm and must transverse a double membrane, consisting of inner and outer membrane bilayers, to be expressed on the cell surface. The outer most layer is comprised of LPS, and both membranes may contain hydrophobic proteins which are required for the transport and surface expression of CPS. Several proteins have been implicated but not defined to be involved in outer membrane transport of capsular polysaccharides, including protein K (Whitfield et al., Membrane proteins correlated with expression of the polysialic acid capsule of *Escherichia coli* K1, *J. Bacteriol.* 161:734–749 (1985)) and Wza (Stevenson et al., Organization of the *Escherichia coli* K12 gene cluster responsible for production of the extracellular polysaccharide colanic acid, *J. Bacteriol.* 178:4885–93 (1996)) of *E. coli*, as well as CtrA of *Neisseria meningitidis* (Frosch et al., Conserved outer membrane protein of *Neisseria meningitidis* involved in capsule expression, *Infect Immun* 60: 798–803 (1992)). We recently have cloned and seqeunced a 1.2 kb open reading frame which we have identified as the wza gene for *V. vulnificus* (Wright et al., submitted) in agreement with recently described nomenclature for bacterial polysaccharide genes (Reeves et al, Bacterial polysaccharide synthesis and gene nomenclature, *Trends Microbiol* 4(12):495–503 1996). We have been able to determine the outer membrane CPS transport function based on the following criteria:

(1) The deduced amino acid sequences of *V. vulnificus* wza and other homologues are consistent with an outer membrane location of the gene product (FIG. 1).

(2) *V. vulnificus* strains with TnphoA insertions in wza exhibit alkaline phosphatase activity (Wright et al., supra 1990). The alkaline phosphatase gene from TnphoA is expressed only in mutants with insertions in genes encoding exported proteins, as a leader sequence is required for expression.

(3) *V. vulnificus* strains with specific, nonpolar mutations in wza do not transport CPS beyond the outer membrane to the cell surface; however, the wza mutants did retain the ability to synthesize CPS and could transport it though the inner membrane. The genes required for expression and transport of bacterial polysaccharides form large multi-gene operons (Roberts et al., Common organization of gene clusters for production of different capsular polysaccharides (K antigens) in *Escherichia coli, J. Bacteriol* 170: 1305–1320 (1988); Bugert and Geider, Molecular analysis of the ams operon required for exopolysaccharide synthesis of *Erwinia amylovora, Mol Microbiol* 15: 917–33 (1995); Comstock et al., Cloning of a region encoding O antigen and capsule of *Vibrio cholerae* 0139 and characterization of the insertion site in the chromosome of *Vibrio cholerae O*1, Mol. Microbiol 19: 815–826 (1996)), and polar mutations into CPS transport genes, such as those introduced by transposons, will disrupt expression of downstream biosynthetic regions. To determine the function of wza gene product in *V. vulnificus*, nonpolar mutations were introduced in order specifically to disrupt expression of the wza without disturbing downstream sequences (Wright et al, submitted). Thus, these mutants demonstrated the CPS transport function of wza gene in *V. vulnificus* and strongly support the outer membrane location of the gene product, as CPS was detected on the inside of the outer membrane.

(4) Further, wza mutants showed decreased virulence in mice, emphasizing the role of the gene product in pathogenesis and its potential as a protective antigen and vaccine candidate.

Purified capsular polysaccharides or polysaccharide-protein conjugates are also the basis for a number of effective vaccines available (Watson et al., Pneumococcal virulence factors and host immune responses to them, *Eur. J. Clin. Microbiol. Infect. Dis Jun*, 14(6):479–90 (1995); Bhatt et al., Meningococcal meningitis, *East Afr. Med J Jan*, 73(1):35–9 (1996); Baker and Kasper, Group B streptococcal vaccines, *Rev Infect Dis* Jul–Aug, 7(4):458–67 (1985); Herbert et al., supra (1995); Kroll et al., Haemophilus influenzae: capsular vaccine and capsulation genetics, *Mol. Med Today Apr*, 2(4):160–5 (1996)).

EXAMPLES

The following examples are given to further illustrate the present invention and are in no way intended to limit the scope of the present invention. Unless otherwise indicated, all parts, percentages, ratios and the like are by weight.

Example 1(a)

Bacterial Stains and Growth Conditions

Most of the *V. Vulnificus* strains used in this invention have been described elsewhere (Wright et al., supra 1990). M06-24/O is an encapsulated isolate with opaque colony morphology and Type I CPS (Hayat et al., Capsular types of *Vibrio vulnificus*: an analysis of strains from clinical and environmental sources, *J. Infect Dis* 168:758–762 (1993) herein incorporated by reference) that was isolated from the blood of an infected individual; M06–24/T is a spontaneous translucent phase variant with reduced CPS expression; CVD752 is an acapsular transposon mutant of M06-24/O which is unable to synthesize CPS; and M06-24/31T produces CPS but does not express capsule on the surface as the result of the interruption in the CPS transport gene, wza (desribed below). Other *V. vulnificus* strains examined include V1015H (Type 1 CPS) and B062316 (Type 2 CPS) and eight other opaque clinical and environmental isolates (Types 2, 3, 4, 5, 8, 12, 14, and 15) whose capsular polysaccharide composition had been previously determined (Hayat et al., supra 1993). Strains were stored at −70° C. in Luria broth (LB, Difco) with 50% glycerol and streaked to LB agar for isolation and subsequent inoculation into LB with or without appropriate antibiotics.

Example 1(b)

Oligonucleotide Probes Specific for Virulent Strains of *V. vulnificus.*

CPS has been shown to be required for virulence in *V. vulnificus*. Transposon mutagenesis was used to identity the CPS locus for *V. vulnificus*. Previously characterized mutants, *V. vulnificus* CVD737 and CVD752, have different TnphoA insertions that produce loss of CPS expression, translucent colony morphology, decreased resistance to the complement-mediated lysis, and reduced virulence in mice (Wright et al., supra 1990). DNA flanking transposon insertions was cloned and sequenced as described below. Synthetic primers (see e.g. FIG. 4), derived from these sequences, were used to recover intact chromosomal DNA of encapsulated parent strain M06-24/O by PCR amplification. Plasmid clones of flanking DNA for transposon insertions in *V. vulnificus* CVD737 and CVD752 were constructed in pBR325 transformed into *E. coli* DH5α (Gibco-BRL) by standard methods (Sambrook et al., supra 1989). These recombinant plasmids were isolated by PEG precipitation and sequenced by cycle-sequencing using dideoxy chain termination (Perkin Elmer) on an automated sequencer (Applied Biosystems, Inc). Sequences were used to construct oligonucleotide primers (UMAB Biopolymer Laboratory) for PCR amplification of the parent strain DNA in order to recover intact parental DNA. DNA from *V. vulnificus* M06-24/O (100 ng) was amplified by PCR using Taq polymerase (Promega) or High Fidelity polymerase (Boehringer Mannaheim) on a thermocycler (MJ Research) under the following conditions: incubation 92° C. for 5 min followed by 35 cycles of 92° C. for 1 min, 57° C. for 2 min and 72° C. for 2 min with a final 10 min extension at 72° C. The region encompassing ORF 2 was amplified by oligonucleotide primers (FIG. 4). PCR products were gel purified by Micropure separators (Amicon) and cloned into either T/A vector pGEMTeasy (Promega) or pBlueScript II (Stratagene). Plasmid DNA or gel-purified PCR products (Amicon) were sequenced as described above. Multiple isolates of plasmid clones were sequenced in both directions. Sequence identity searches and alignments were done with either Tfasta or fasta from (GCG Wisconsin Package) or Blast (Entrez). Chromosomal DNA was extracted with Quiamp Tissue Extraction kits (Quiagen) and digested with restriction enzymes (Promega). DNA was visualized on 0.5 to 1.0% agarose gels with ethidum bromide and transferred to Zetaprobe GT (Biorad) nylon membranes using alkaline transfer in 0.4 M NaOH. A Not I digest of pACW36, which included all of the *V. vulnificus* wza insert, was gel purified as described above, labeled with $^{32}P$ by random priming (Amersham), and used for probing. Membranes were hybridized in phosphate buffer with 7% SDS and washed under stringent conditions at 65° C. in SSC with decreasing amounts of SDS, and visualized by autoradiography.

Two complete open reading frames (ORF1 and ORF2) were identified with homology to known genes required for CPS transport. Regulatory regions, which include a putative promoter and the ops element highly associated with CPS operons (Nieto et al., Suppression of transcription polarity in the *Escherichia coli* haemolysis operon by a short upstream element shared by polysaccharide and DNA transfer determinants, *Mol Microbiol* 19:705–713 (1996)), were found upstream of these ORFs and are shown in FIGS. 1 and 2. In agreement with recently described nomenclature for bacterial polysaccharide genes (Reeves et al, supra 1996), we have identified *V. vulnificus* ORF2 as the wza gene for this species. Genbank searches showed *V. vulnificus* ORF2 had greatest DNA (64%) and amino acid (60%) identity and similarity (88%) with ORF4 from the cps locus of *Klebsiella pneumoniae* (Arakawa et al., Genomic organization of the *Klebsiella pneumoniae* cps region responsible for serotype K2 capsular polysaccharide synthesis in the virulent strain Chedid, *J. Bacteriol* 177: 1788–1769 (1995)), which was originally described as a homologue of Group II-like CPS transport gene bexD of *Haemophilus influenzae* (Kroll et al., The bex locus in encapsulated *Haemophilus influenzae* type b, Mol. Micro 4: 1853–1862 (1990)). However, *K. pneumoniae* ORF4 is currently considered a member of a gene family which does not include bexD but does encompass the wza gene for *E. coli* colanic acid CPS (Stevenson et al., supra, *J. Bactiol* 178:4885–4893 (1996)), amsH of *Erwinia amylovora* (Bugert and Geider, supra 1995), epsA of *Pseudomonas solanacearum* (Huang and Schell, Molecular characterization of the eps gene cluster of *Psuedomonas solanacearum* and its transcriptional regulation at a single promoter, *Mol. Microbiol* 16: 677–689 (1995)), and exoF of *Rhizobium meliloti* (Reuber and Walker, Biosynthesis of succinoglycan, a symbiotically important exopolysaccaride of *Rhizobium meliloti, Cell* 74(2): 269–280 (1993)).

Example 1(c)

Relationship of *V. vulnificus wza* to CPS Expression

To determine the function of the wza gene product, nonpolar mutations (Menard et al., Nonpolar mutagenesis of the ipa genes defines IpaB, IpaC and IpaD as effectors of *Shigella flexneri* entry into epithelial cells, *J. Bacteriol* 175(18):5899–5606 (1993) herein incorporated by reference) were introduced into the SphI site of wza in both an in-frame and a +1 orientation and recombined into the chromosome of *V. vulnificus* M06-24/O to generate strains M06-24/31T and M06-24/32T, respectively. Clones for marker exchange were derived from pACW15 and constructed by insertion into a unique SphI site wza with kanamycin cassettes, which previously had been used to introduce nonpolar mutations in the ipa genes of *S. flexneri* (Menard et al., supra 1993). Cassettes are on a SmaI fragment of 850 bp or 851 bp, with or without an additional base at the 3' end, and include start and stop codons and ribosomal binding site. Cassettes were introduced into in the ORF2 by blunt end ligation to create either in-frame (pACW731) or a +1 frame shift (pACW732) nonpolar mutations. The broad host range vector, pRK404, was used for plasmid constructs that were transformed into conjugation-competent *E. coli* strain for conjugation into *V. vulnificus*. Crossover events were facilitated by the introduction of another plasmid (pR751, provided by J. Kaper) from the same incompatibility group (IncP) with dual selection for the inserted kanamycin marker and trimethoprim resistance from the IncP phasmid. About 50% of the resulting transconjugants were positive for the crossover events, as determined by acquisition of translucent phenotype, and insertions were confirmed by PCR and Southern analysis. Insertions of the kanamycin cassette were confirmed by Southern analysis, as indicated by increased size of a HindIII fragment in mutants (5.8 kb) in comparison to that of the parental strain (5.0 kb). Both mutants exhibited the translucent phenotype and did not revert to the opaque colony morphology when grown with or without antibiotic selection.

CPS-specific monoclonal antibody (7/G4-D2, Wright et al., submitted to Infect. Immun.) was used for ELISA analysis of the CPS content of both membrane and soluble fractions. To produce monoclonal antibody, *V. vulnificus* M06-24/O CPS was extracted (Reddy et al., Capsular polysaccharide structure of a clinical isolate of *Vibrio vulnificus* strain BO62316 determined by heteronuclear NMR spectroscopy and high-performance anion-exchange chromatography, *Anal. Biochem* 214: 105–115 1992) and conjugated to tetanus toxoid as previously described (Devi et al., Synthesis and immunochemical characterization of capsular polysaccharide-protein conjugate vaccines of *Vibrio vulnificus, Infect Immun* 64:2220–2224 1995) Briefly, BALB/c mice (Charles River, Wilmington, Mass.) were immunized intraperitoneally (IP) with one of two CPS conjugates, VvPSTT-a or VvPSTT-b, prepared by conjugating tetanus toxoid to *V. vulnificus* CPS, using either carboxyl or hydroxyl activation of the polysaccharide, respectively. Antigen for inoculations was diluted 1:5 in phosphate buffered saline (PBS, pH 7) and mixed with an equal volume of Freund's complete adjuvant. Animals were boosted at about 4 weeks post inoculation with antigen and Freund's incomplete adjuvant and at 8 weeks with antigen alone. Three to five days after the final boost, spleens were removed and processed by mechanical shearing. Splenocytes were mixed 10:1 with SP2/O cells in the presence of polyethylene glycol 4000. Plated cells were incubated at 37° C. in 5% $CO_2$ in the presence of hypoxanthine-aminopterin-thymidine until colonies had grown. Supernatants were collected and tested for reactivity against live M06-24/O cells and purified CPS by ELISA (described below). Following limiting dilution cloning of selected cell lines, CPS-reactive monoclonal antibodies were isotyped (MabCheck, Sterogene Bioseparations, Inc., Arcadia, Calif.), and specificity was examined by ELISA or western blot analyses as described below. Based on their high reactivity to purified CPS from *V. vulnificus* M06-24/O, hybridomas cell lines 7/G4-D2 (IgA derived from VvPS-TTb), 1004-B7 (IgG3 derived form VvPS-TTa) or 1002-C4 (IgM derived from VvPS-TTa) were selected for subsequent studies. Purified *V. vulnificus* CPS and LPS preparations were analyzed on discontinuous SDS-PAGE as described by Laemmli, Cleavage of structural protein during assembly of the head of bacteriophage T-4, *Nature* 227:680–95 (1970) and compared to molecular weight standards (Bio-Rad laboratories, Hercules, Calif.). Gels were silver stained for LPS or transferred to nitrocellulose membrane for Western analysis. Western blots were incubated with primary antibody (either polyclonal anti-*V. vulnificus* M06-24/O whole cell or monoclonal 7/G4-D2 antibody) diluted in blocking buffer consisting of 5% milk with 150 mM NaCl, 50 mM Tris-HCl, pH 7.5 for 2 h at 4° C. with shaking. The secondary antibody alkaline phasphatase labeled Goat anti-rabbit or anti-mouse immunoglobulin was diluted in blocking buffer and incubated with membranes for 1 h at room temperature with shaking, followed by development in buffered substrate of 5-bromo-4-chloro-3-indolyl phosphate and nitroblue tetrazolium.

Whole cell ELISA was used to determine CPS expression in *V. vulnificus* strains. Bacterial strains described above were grown in LB to mid-log ($OD_{600}$=0.7) and washed once in PBS and diluted to an initial concentration of $10^7$ cells/well. Two-fold serial dilutions of these cells were prepared in triplicate in 96-well microtiter plates (Immulon 1, Dynotech) and incubated at 4° C. overnight to bind cells to the plates. Excess antigen was removed by washing with 20% Tween in PBS, followed by blocking of unbound sites with PBS containing 5% fetal bovine serum (FBS, Gibco BRL) at 37° C. for 1 h. Hybridoma supernatants were diluted 1:20 in PBS-1% FBS, 100 µl added to wells, and the plates incubated for 1 h at 37° C. After washing plates as above, 100 µl alkaline phosphatase-labeled goat-anti-mouse polyclonal antibody diluted 1:1000 in PBS with 1% FBS (Kirkegaard and Perry, Gaithersburg, Md.) was added to all wells and incubated as before. The plates were washed a final time, substrate (Kirkegaard and Perry, Gaithersburg, Md.) added to all wells, and $A_{405}$ determined after 30 min incubation at 37° C. Negative controls for whole cell and cell fractions of each strain employed the above method without primary antibody, and the mean $A_{405}$ of these samples was subtracted from the experimental value to determine the binding of CPS-specific antibody.

Immunoelectron microscopy (IEM) was used to visualize CPS production of *V. vulnificus* strains. *V. vulnificus* were embedded, immunolabeled and observed by transmission electron microscopy as previously described. Briefly, cells grown overnight at 30° C. on L agar were washed in 3.5% saline, pelleted by centrifugation (2,000×g, 15 min., 4° C.), fixed, and embedded in LR White. Ultrathin sections were collected on nickel grids (Electron Microscopy Sciences, Fort Washington, Pa.) which were incubated specimen side down in 5% goat serum in PBS (GS/PBS) for 15 min and immunolabeled for 1 h with anti-CPS monoclonal antibody from hybridoma supernatants diluted 1:1 in GS/PBS. Grids were washed in GS/PBS with subsequent 15 min incubation in secondary antibody conjugate (goat anti-mouse IgA labeled with 10 nm colloidal gold) diluted 1:50 in GS/PBS, followed by multiple washes in $dH_2O$. Cells were negatively stained with 2% uranyl acetate for 5 min., followed by 0.2% lead citrate staining for 1 min. Observations were performed on a JEM-100 CX II transmission electron microscope (80 kV; JEOL Ltd., Tokyo, Japan).

ELISA analysis confirmed that CPS was detectable in membrane fractions of sonicates of wza mutants and exceeded concentrations of the translucent phase variant. These data indicate that nonpolar CPS transport mutants retained the ability to synthesize CPS without loss of epitope. To confirm the role of the wza gene in CPS expression, we further examined *V. vulnificus* strains by immunoelectron microscopy (IEM). Monoclonal antibody bound the surface of the encapsulated parent strain, appearing to emanate in discrete strands from the OM. As expected, the opaque phase variant exhibited surface expression of CPS to a much greater extent than the translucent variant, and acapsular CVD752 did not bind antibody. *V. vulnificus* wza mutant M06-24/31T also did not bind antibody on the cell surface, but CPS was detected consistently in the cytoplasm and at the OM. IEM results are further supported by analysis using flow cytometry and the same CPS-specific monoclonal antibody, which demonstrated loss of surface CPS expression in M024-31T wza mutant in that histograms were identical to that of acapsular CVD752 (Wright et al., submitted to Infect. Immun.). Loss of CPS cell surface expression in nonpolar wza mutant, *V. vulnificus* M06-24/31T, demonstrates that this gene is required for transport of the polysaccharide to the cell surface and constitutes the first experimental evidence to link the expression of wza gene to CPS transport function.

Primers derived from *V. vulnificus* M06-24/0 sequence were used to PCR amplify chromosomal DNA from virulent (opaque) or avirulent (translucent) phase variants of *V. vulnificus* strains M06-24, LC4, 345, E4125. PCR products included ORF1, ORF2, and more than 500 bases upstream of the CPS locus. Products of identical size were observed for all strains except the translucent variant *V. vulnificus* 345/T (the only environmental isolate), which did not amplify with these or nested primers. Southern analysis (FIG. 3) confirmed deletion of wza in *V. vulnificus* 345/T and also revealed a smaller deletion or restriction site polymorphism in this region for the translucent phase variant of strain LC4. No differences in restriction fragment length were detected between the phase variants of *V. vulnificus* M06-24 and E4125, although restriction fragment length polymorphism was observed among the strains. However, DNA sequencing of wza genes and upstream sequences revealed only minor, i.e., 1 or 2 bases, differences among phase variants.

Additional environmental isolates identified as *V. vulnificus* by species-specific VVAP probe (Wright et al., 1993)

were subsequently examined for the presence of wza based on hybridization with an oligonucleotide probe (712 A, FIG. 4). The majority (88%) of opaque and presumably encapsulated isolates (n=97) were positive for the wza probe, indicating a high degree of conservation of this gene among *V. vulnificus* environmental isolates. Strains that were wza probe-negative included both opaque and translucent phase variants. However, a significantly greater percentage of translucent strains (50%, n=10) than opaque strains were wza negative, suggesting a higher rate of deletions or rearrangements in wza than that observed for opaque isolates (Fisher's Exact test, 2 tail, p=0.007.) Phase variation in CPS expression is common, and has been attributed to insertional inactivation of CPS genes by IS elements or deletion mutations (Ou et al., Specific insertion and deletion of insertion sequence 1-like DNA element causes the reversible expression of the virulence capsular antigen Vi of *Citrobacter freundii* in *Escherichia coli, Pro Natl Acad Sci USA* 85:4402–4405 (1988); Kroll et al., An ancestral mutation enhancing the fitness and increasing the virulence of *Haemophilus influenzae* type b, *J. Infect Dis* 168: 172–176 (1993)). Deletion or rearrangement was observed for 2 or 4 translucent phase variant, and wza probe-negative isolates were significantly more frequent among translucent than opaque environmental phase variants, suggesting a possible recombination-mediated mechanism for phase variation. Although wza-negative opaque isolates were observed, the criteria for species identification was based solely on the WAP probe and further studies are on-going to confirm the identity of these strains and assay their virulence.

Example 2

WZA Protein Expression

The cloned *V. vulnificus* wza gene can be used to produce the transcribed mRNA sequence that can be translated into protein, using either expression vectors in *E. coli* or in vitro transcription/translation systems. An example of one of these transcription/translation systems is the Xpress™ System (Invitrogen Corp., CA) in which the wza gene from *V. vulnificus* is cloned into a baculovirus transfer vector according to the maunfacturer's instructions. As the protein is expressed six tandem histidine residues are fused to the N-terminus of the protein. These residues then can bind tightly to a nickel-chelating resin which allows an effective means to purify the expressed wza protein. The protein can finally be released from the histidine tag by treating the chelating resin with an enterokinase. Wza protein expressed and purified by such a method is then suitable for other applications such as the production of polyclonal and monoclonal antibodies.

Example 3

Detection of *V. vulnificus* Using DNA Probes

Gene probes from nucleic acid sequences derived from the wza gene can be used to detect *V. vulnificus* in environmental samples for example as described by Wright et al., 1993, supra. Briefly, oysters homogenates are prepared by blending 3–12 shucked oysters in Dulbecco's phosphate buffered saline (DPBS) in a Waring blender for 90s. Following serial dilution of the homogenates in DPBS, subsamples are plated on non-selective medium (L-agar) and *V. vulnificus* selective agar. After incubation of the plates at room temperature resultant bacterial colonies are overlaid with #541 Whatman filter paper for 30 min. Filters are then placed onto Whatman #3 filter saturated with lysing solution (0.5N NaOH, 1.5M NaCl) and then placed in a microwave (on High) for 60–120s. Rotate the filters 90° and repeat. Filters are than placed on #3 filter paper pre-wet with 2M ammonium acetate buffer and incubated at room temperature for 5 min. Briefly rinse the filter(s) in 2×SSC (0.15M NaCL, 0.015M NaCitrate, pH 7.0) and then treat with proteinase K solution (40 μg/ml Prot.K in 1×SSC) for 30 min at 42° C. with shaking. Filters are then washed 3 times for 10 min. each in SSC and then placed in hybridization buffer (bovine serum albumin (BSA) 0.5 g, sodium lauryl sulfate (SDS) 1.0 g, polyvinylpyrrolidone (PVP) 0.5 g in 100 ml 1×SSC) for 30 min at 56° C. with shaking (50 rpm). After incubation, remove the buffer and replace with fresh hybridization solution containing the labeled probe (in this example the probe is labeled with alkaline phosphatase) and incubate for a further hour at 56° C. with shaking. Filters are then washed 2×10 min. in SSC/SDS buffer (1% SDS in 1×SSC) at 56° C., 3×5 min 1×SSC and finally 2×5 min. in diethanolamine (DEA) buffer (DEA 19.3 ml, 2M $MgCl_2$ 5.0 ml, $NaN_3$ 0.4 g in 2.0 l $dH_2O$ pH 9.5). Probe positive colonies ie. *V. vulnificus* are visualized by the incubation of the filters in DEA buffer containing nitro blue tetrazolium (NBT, 75 mg/ml in 70% dimethylformamide) and 5-bromo-4-chloro-3-indoyl phosphate (BCIP, 50 mg/ml in dimethylformamide) in a light-resistant container at room temperature with shaking. Progress of color development is checked regularly and when at the desired level (with minimal background signal) the filters are rinsed 3×10 min in tap water. *Vibrio vulnificus* colonies are easily distinguished on the filters as dark blue/purple colonies.

Example 4

Detection of *V. vulnificus* Using PCR

Primers derived from the wza gene sequence can be used to identify *V. vulnificus* in a variety of biological (environmental and clinical) samples. An example is the use of the polymerase chain reaction to identify *V. vulnificus* in oysters. DNA is prepared from oyster homogenates (see example 3 above) as described by Boccuzzi et al., Preparation of DNA extracted from environmental water samples for PCR amplification *J. Microbiol Methods* 31: 193–199 (1998) herein incorporated by reference. Briefly, oyster homogenates (1 ml) are collected by centrifugation and the cell pellet washed twice with physiological saline. The pellet is resuspended in 25 μl of 5.9M guanidine isothiocyanate (GITC) to disrupt the cells. After incubation of the samples at 60° C. for up to 90 min., the samples were diluted with sterile deionized water to give a final concentration of 0.3M GITC. This lysate was then extracted twice with chloroform and finally the DNA was precipitated with 95% ethanol at −20° C. in the presence of 0.3M sodium acetate. Resultant DNA is then used as the template in the PCR. Primers selected from the wza gene sequence (derived using commercial computer programs such as Gene Jockey II, MacVector and Primer Design III) are then used in the PCR to amplify specific wza sequences. An example of conditions that may be used are those using forward primer 712A and reverse primer 752J (FIG. 4). DNA is amplified by PCR using Taq polymerase (Promega) or High Fidelity polymerase (Boehringer Mannheim) under the following conditions: incubation 92° C. for 5 min followed by 35 cycles of 92° C. for 1 min, 57° C. for 2 min and 72° C. for 2 min with a final 10 min extension at 72° C. Amplified DNA is visualized on an agarose gel stained with ethidium bromide.

Example 5

Creation of *V. vulnificus* Specific Antibody

Purified Wza protein can be used for the preparation of polyclonal and monoclonal antibodies using techniques known in the art (Harlow and Lane 1988, supra). Polyclonal antibodies to the Wza protein are produced in New Zealand White rabbits by immunizing the animal subcutaneously with 500 μg purified protein mixed with Freund's complete adjuvant (0.5 ml). Four-six weeks later a second immunization is given subcutaneously with the protein suspended in Freund's incomplete adjuvant and repeated a further four-six weeks later. At the end of the immunization period, animals are anesthetized and exsanguinated. Collected blood is allowed to clot at room temperature for 1 hour followed by incubation at 4° C. overnight to allow the clot to retract. The resultant serum containing polyclonal antibody is collected by pipette, transferred to sterile tubes and stored at −20° C.

Monoclonal antibodies can be made to purified Wza protein by immunizing BALB/c mice intraperitoneal with 20 μg purified protein suspended in Freund's complete adjuvant (0.2 ml). Antibody titers are assessed three to four weeks later, followed by an antigen boost delivered intraperitoneally (IP) in Freund's incomplete adjuvant. Three—four weeks later the antibody titer is determined again and if a sufficient increase in titer has occurred the final antigen boost is given intravenously (IV). Three days later the spleen from an immunized mouse is removed and the cells released by mechanical shearing into culture medium. Splenocytes are mixed 10:1 with SP2/O (mouse myeloma ) cells in the presence of polyethylene glycol 4000. Plated cells are incubated at 37° C./5% $CO_2$ in the presence of hypoxanthine-aminopterin-thymidine (HAT) until colonies have grown. Supernatants from growing hybridomas are collected and tested for reactivity against the purified protein by immunoassay. Cell lines producing antibody reactive with the purified protein are cloned by limiting dilution.

Although certain presently preferred embodiments of the invention have been described herein, it will be apparent to those skilled in the art to which the invention pertains that variations and modifications of the described embodiment may be made without departing from the spirit and scope of the invention. Accordingly, it is intended that the invention be limited only to the extent required by the appended claims and the applicable rule of law.

What is claimed is:

1. A nucleotide sequence which hybridizes preferentially to the nucleic acid sequence shown in FIG. 1 (SEQ ID NO 1), or a fragment of said nucleic acid sequence, under appropriate hybridization conditions, said nucleotide sequence being about 20–50 bases in length and wherein hybridization of said nucleotide sequence is an indication of strains of *V. vulnificus*.

2. The nucleotide sequence of claim 1 wherein said nucleotide sequence has a lack of internal repeats.

3. The nucleotide sequence of claim 1 wherein said nucleotide sequence is one of a pair of PCR primers.

4. A probe comprising the nucleotide sequence of claim 1 and a detectable moiety.

5. A method of detecting the presence of *V. vulnificus* in a sample comprising the steps of:

(a) contacting the sample with the nucleotide sequence of claim 1;

(b) imposing hybridization conditions on the sample and said nucleotide sequence to allow the formation of a hybridization product between said nucleotide sequence and DNA or RNA from *V. vulnificus*; and (c) detecting any hybridization product as an indication of the presence of *V. vulnificus* in the sample.

6. The nucleotide sequence of claim 1 wherein said nucleotide sequence hybridizes under stringent conditions to the wza gene of *V. vulnificus*.

7. A kit for detecting the presence of *V. vulnificus* in a sample comprising (a) a pair of PCR primers according to claim 3, (b) a suitable polymerase, and (c) buffers and reagents usable in PCR.

8. The probe according to claim 4 wherein the detectable moiety is selected from the group consisting of biotin, an enzyme, and a fluorescent molecule.

9. The probe according to claim 8 wherein the detectable moiety is a fluorescent molecule selected from the group consisting of fluorescein and rhodamine.

10. An isolated nucleotide sequence which hybridizes preferentially to the capsular polysaccaride transport gene from *V. vulnificus*, said nucleotide sequence being about 20–50 bases in length.

11. The nucleotide sequence of claim 10 wherein said nucleotide sequence is or is complementary to a nucleotide sequence consisting of about 20–50 consecutive nucleotides from a nucleotide sequence shown in FIG. 1 (SEQ ID NO 1).

12. The nucleic acid sequence shown in FIG. 1 (SEQ ID NO 1) in isolated form.

* * * * *

SEQUENCE LISTING

<160> NUMBER OF SEQ ID NOS: 14

<210> SEQ ID NO 1
<211> LENGTH: 2499
<212> TYPE: DNA
<213> ORGANISM: Vibrio vulnificus

<400> SEQUENCE: 1
gtgtacagcc gcctgtggat cccgcatacg cgggaatgac agttgggggc gtggcggcgg 60
tgtgctgagt tttttgttct ttgccgctga acttagctct gctttttctt ttcttatttt 120
tgtcatcctc gcgaacgcgg ggaaccatcc gtcagcaccc gccatcacta actttgaaca 180
caacaatccc agcaacttac gttcactttc cctaaaaaca aaaaagccaa cactctttca 240
agtgttggct tagagactaa agcactaaaa cttagttagt accagtagta ccagtagtac 300
cagtagtgtt gtttgaagaa acaacaactg ctgttgccgc tactgctgca cctgccgcta 360
ctgctgcagt tgttgctgca cccgcgctag ctgcacctgc gccagcacct gctgctgcgc 420
ctgtagaagc agttgtacta gttgctgtag ttgctgttgc agcttcaccc gcagcaaatg 480
cagtagaaga tacacctagt gcaatcaacg ctgctaatgc gattttttttc atgattattc 540
ctttgtatat atacgttttc aaacatcgat gtcggaactt taatagctcc ggtgtttatt 600
ttaggtagaa tttgggcgga atgtaaacaa ttagttgtag ctgcagcgat gtgaatttat 660
ggtttttatc tcattgatag taccgtttgc ttagcaaaaa caattgtgct ctaagccaca 720
atatggataa tatccgccca tgattaatat taataatgac acaatactca gtgtgtcata 780
aaacgtcagt actttgttgc agcaagccat tagagctatt gcgcagcaaa ttgtcccagc 840
gctatgtggt tttgcgtgct taccaaaggg cggtagcgtg tcaaaaaagc cacaaatatg 900
ggtggaaaac cacactttta acgggttctt acattttctt acgttcagtt agcgtagaat 960
gttgtgcgaa gctgcttaaa atcgcagtca gtgtgggagc taggctataa agtatagtta 1020
aatgcggtta aggaaaacgc ctttaactat gttgaatacc tatgctttca aaagcgttag 1080
aaagaaatgg tgttcaatcg aacctttgct cattcaagag tgccgtaaac actcttaatt 1140
tagacgattt ggcttacatg gaactaaaaa caaaacttct gctagcgatg ctagcgcctg 1200
ccttgcttgc cggttgtact gtacccggct cacatctatc catcgataat aaaaaccttg 1260

-continued

```
ttgaagtgaa cgatagcagc caagaaagta acctttctga ggtggttaat ctgtatccgc   1320
taaacgctca atcggtcacg gaatacgcca aagcgcagca ttttgcttct cgcgcaaacc   1380
cagaacttga tctgcagatc gcccgttatg aatacaaagt gggccctggc gacattctta   1440
acgttaccat ttgggatcac cctgagttga cgattccagc aggctcttac cgtagtgcat   1500
ccgaagtagg taactgggtg catgcagatg gcaccatttt ctacccttac attggcactg   1560
tagaagtggc agataaaaca gtgcgtgaga tccgcgccga tattgccaaa cgtcttgcga   1620
agtttattga aagcccacag gtcgatgtca acgtagccgc gttccgctct aagaaagctt   1680
acattaccgg tgaagttgaa aaaccaggcc aacaagccat caccaatatc cctttaacca   1740
ttctggatgc tgtaaaccgt gctggtggtc tagcggaaga tgccgattgg cgcaacgtga   1800
cgcttactcg caatggtgaa gagcaagcca tttctcttta cgcgcttatg cagcgtggtg   1860
atttaacgca aaaccgttta ttagagccgg gcgatatcat ccacgtgcca cgcaacgaca   1920
gccaaaaagt gtttgtaatg ggcgaagtaa aagatcccaa actgcttaaa atggatcgct   1980
ctggcatgag cctgacggaa gccctcagca gcgttggggg aatcaacgag ctctctgccg   2040
atgcaacggg cgtgttcgtt atccgtacgt cagacaacaa atctgaacgc atggcggata   2100
tctaccagct caacattaaa gatgcctctg cactagtgat tggcacagaa ttcgatctaa   2160
aaccatacga tatcgtctat gtgaccgccg cacctattac tcgatggaat cgtgtgatca   2220
gtcagttaat gccaacgatt tatggcttta atgaactaac tgaaggtgct ctacgcgtta   2280
aaacgtggcc gtaagatgat ttaaaagcgg tcctatggcc cttgggtcct aggggctaat   2340
ggattggata agtctcgtgt aagcaaggat ggctgatgag ggttttggga tttgaaaggc   2400
ttgaagtatg gaaaaagagt tcaagacttt ctgttgatat cgtcaaagcc cttcatcgct   2460
gtaaaaacta tgcattggtt gatcagataa cgcgaagtt                          2499
```

<210> SEQ ID NO 2
<211> LENGTH: 410
<212> TYPE: PRT
<213> ORGANISM: Vibrio vulnificus

<400> SEQUENCE: 2

```
Met Leu Ser Lys Ala Leu Glu Arg Asn Gly Val Gln Ser Asn Leu Cys
  1               5                  10                  15

Ser Phe Lys Ser Ala Val Asn Thr Leu Asn Leu Asp Asp Leu Ala Tyr
             20                  25                  30

Met Glu Leu Lys Thr Lys Leu Leu Leu Ala Met Leu Ala Pro Ala Leu
         35                  40                  45

Leu Ala Gly Cys Thr Val Pro Gly Ser His Leu Ser Ile Asp Asn Lys
     50                  55                  60

Asn Leu Val Glu Val Asn Asp Ser Ser Gln Glu Ser Asn Leu Ser Glu
 65                  70                  75                  80

Val Val Asn Leu Tyr Pro Leu Asn Ala Gln Ser Val Thr Glu Tyr Ala
                 85                  90                  95

Lys Ala Gln His Phe Ala Ser Arg Ala Asn Pro Glu Leu Asp Leu Gln
            100                 105                 110

Ile Ala Arg Tyr Glu Tyr Lys Val Gly Pro Gly Asp Ile Leu Asn Val
        115                 120                 125

Thr Ile Trp Asp His Pro Glu Leu Thr Ile Pro Ala Gly Ser Tyr Arg
    130                 135                 140

Ser Ala Ser Glu Val Gly Asn Trp Val His Ala Asp Gly Thr Ile Phe
```

-continued

```
145                 150                 155                 160

Tyr Pro Tyr Ile Gly Thr Val Glu Val Ala Asp Lys Thr Val Arg Glu
                165                 170                 175

Ile Arg Ala Asp Ile Ala Lys Arg Leu Ala Lys Phe Ile Glu Ser Pro
            180                 185                 190

Gln Val Asp Val Asn Val Ala Ala Phe Arg Ser Lys Lys Ala Tyr Ile
        195                 200                 205

Thr Gly Glu Val Glu Lys Pro Gly Gln Gln Ala Ile Thr Asn Ile Pro
    210                 215                 220

Leu Thr Ile Leu Asp Ala Val Asn Arg Ala Gly Gly Leu Ala Glu Asp
225                 230                 235                 240

Ala Asp Trp Arg Asn Val Thr Leu Thr Arg Asn Gly Glu Glu Gln Ala
                245                 250                 255

Ile Ser Leu Tyr Ala Leu Met Gln Arg Gly Asp Leu Thr Gln Asn Arg
            260                 265                 270

Leu Leu Glu Pro Gly Asp Ile Ile His Val Pro Arg Asn Asp Ser Gln
        275                 280                 285

Lys Val Phe Val Met Gly Glu Val Lys Asp Pro Lys Leu Leu Lys Met
    290                 295                 300

Asp Arg Ser Gly Met Ser Leu Thr Glu Ala Leu Ser Ser Val Gly Gly
305                 310                 315                 320

Ile Asn Glu Leu Ser Ala Asp Ala Thr Gly Val Phe Val Ile Arg Thr
                325                 330                 335

Ser Asp Asn Lys Ser Glu Arg Met Ala Asp Ile Tyr Gln Leu Asn Ile
            340                 345                 350

Lys Asp Ala Ser Ala Leu Val Ile Gly Thr Glu Phe Asp Leu Lys Pro
        355                 360                 365

Tyr Asp Ile Val Tyr Val Thr Ala Ala Pro Ile Thr Arg Trp Asn Arg
    370                 375                 380

Val Ile Ser Gln Leu Met Pro Thr Ile Tyr Gly Phe Asn Glu Leu Thr
385                 390                 395                 400

Glu Gly Ala Leu Arg Val Lys Thr Trp Pro
                405                 410


<210> SEQ ID NO 3
<211> LENGTH: 540
<212> TYPE: DNA
<213> ORGANISM: Vibrio vulnificus
<220> FEATURE:
<221> NAME/KEY: CDS
<222> LOCATION: (97)..(348)
<220> FEATURE:
<221> NAME/KEY: CDS
<222> LOCATION: (403)..(540)

<400> SEQUENCE: 3

tggtttttat ctcattgata gtaccgtttg cttagcaaaa acaattgtgc tctaagccac     60

aatatggata atatccgccc atgattaata ttaata atg aca caa tac tca gtg      114
                                        Met Thr Gln Tyr Ser Val
                                          1               5

tgt cat aaa acg tca gta ctt tgt tgc agc aag cca tta gag cta ttg      162
Cys His Lys Thr Ser Val Leu Cys Cys Ser Lys Pro Leu Glu Leu Leu
            10                  15                  20

cgc agc aaa ttg tcc cag cgc tat gtg gtt ttg cgt gct tac caa agg      210
Arg Ser Lys Leu Ser Gln Arg Tyr Val Val Leu Arg Ala Tyr Gln Arg
        25                  30                  35

gcg gta gcg tgt caa aaa agc cac aaa tat ggg tgg aaa acc aca ctt      258
```

-continued

```
Ala Val Ala Cys Gln Lys Ser His Lys Tyr Gly Trp Lys Thr Thr Leu
     40                  45                  50

tta acg ggt tct tac att ttc tta cgt tca gtt agc gta gaa tgt tgt      306
Leu Thr Gly Ser Tyr Ile Phe Leu Arg Ser Val Ser Val Glu Cys Cys
 55                  60                  65                  70

gcg aag ctg ctt aaa atc gca gtc agt gtg gga gct agg cta              348
Ala Lys Leu Leu Lys Ile Ala Val Ser Val Gly Ala Arg Leu
                 75                  80

taaagtatag ttaaatgcgg ttaaggaaaa cgcctttaac tatgttgaat acct atg      405
                                                            Met
                                                             85

ctt tca aaa gcg tta gaa aga aat ggt gtt caa tcg aac ctt tgc tca      453
Leu Ser Lys Ala Leu Glu Arg Asn Gly Val Gln Ser Asn Leu Cys Ser
                 90                  95                 100

ttc aag agt gcc gta aac act ctt aat tta gac gat ttg gct tac atg      501
Phe Lys Ser Ala Val Asn Thr Leu Asn Leu Asp Asp Leu Ala Tyr Met
            105                 110                 115

gaa cta aaa aca aaa ctt ctg cta gcg atg cta cgg cct                  540
Glu Leu Lys Thr Lys Leu Leu Leu Ala Met Leu Arg Pro
        120                 125                 130


<210> SEQ ID NO 4
<211> LENGTH: 130
<212> TYPE: PRT
<213> ORGANISM: Vibrio vulnificus

<400> SEQUENCE: 4

Met Thr Gln Tyr Ser Val Cys His Lys Thr Ser Val Leu Cys Cys Ser
  1               5                  10                  15

Lys Pro Leu Glu Leu Leu Arg Ser Lys Leu Ser Gln Arg Tyr Val Val
            20                  25                  30

Leu Arg Ala Tyr Gln Arg Ala Val Ala Cys Gln Lys Ser His Lys Tyr
        35                  40                  45

Gly Trp Lys Thr Thr Leu Leu Thr Gly Ser Tyr Ile Phe Leu Arg Ser
     50                  55                  60

Val Ser Val Glu Cys Cys Ala Lys Leu Leu Lys Ile Ala Val Ser Val
 65                  70                  75                  80

Gly Ala Arg Leu Met Leu Ser Lys Ala Leu Glu Arg Asn Gly Val Gln
                 85                  90                  95

Ser Asn Leu Cys Ser Phe Lys Ser Ala Val Asn Thr Leu Asn Leu Asp
            100                 105                 110

Asp Leu Ala Tyr Met Glu Leu Lys Thr Lys Leu Leu Leu Ala Met Leu
        115                 120                 125

Arg Pro
    130


<210> SEQ ID NO 5
<211> LENGTH: 84
<212> TYPE: PRT
<213> ORGANISM: Vibrio vulnificus

<400> SEQUENCE: 5

Met Thr Gln Tyr Ser Val Cys His Lys Thr Ser Val Leu Cys Cys Ser
  1               5                  10                  15

Lys Pro Leu Glu Leu Leu Arg Ser Lys Leu Ser Gln Arg Tyr Val Val
            20                  25                  30

Leu Arg Ala Tyr Gln Arg Ala Val Ala Cys Gln Lys Ser His Lys Tyr
        35                  40                  45
```

-continued

```
Gly Trp Lys Thr Thr Leu Leu Thr Gly Ser Tyr Ile Phe Leu Arg Ser
     50                  55                  60

Val Ser Val Glu Cys Cys Ala Lys Leu Leu Lys Ile Ala Val Ser Val
 65                  70                  75                  80

Gly Ala Arg Leu


<210> SEQ ID NO 6
<211> LENGTH: 46
<212> TYPE: PRT
<213> ORGANISM: Vibrio vulnificus

<400> SEQUENCE: 6

Met Leu Ser Lys Ala Leu Glu Arg Asn Gly Val Gln Ser Asn Leu Cys
  1               5                  10                  15

Ser Phe Lys Ser Ala Val Asn Thr Leu Asn Leu Asp Asp Leu Ala Tyr
             20                  25                  30

Met Glu Leu Lys Thr Lys Leu Leu Leu Ala Met Leu Arg Pro
         35                  40                  45


<210> SEQ ID NO 7
<211> LENGTH: 21
<212> TYPE: DNA
<213> ORGANISM: Vibrio vulnificus

<400> SEQUENCE: 7

attccgtgac cgattgagcg t                                                 21


<210> SEQ ID NO 8
<211> LENGTH: 20
<212> TYPE: DNA
<213> ORGANISM: Vibrio vulnificus

<400> SEQUENCE: 8

tgcagcaagc cattagagct                                                   20


<210> SEQ ID NO 9
<211> LENGTH: 20
<212> TYPE: DNA
<213> ORGANISM: Vibrio vulnificus

<400> SEQUENCE: 9

ccagcaactt acgttcactt                                                   20


<210> SEQ ID NO 10
<211> LENGTH: 20
<212> TYPE: DNA
<213> ORGANISM: Vibrio vulnificus

<400> SEQUENCE: 10

tcgcgttatc tgatcaacca                                                   20


<210> SEQ ID NO 11
<211> LENGTH: 2499
<212> TYPE: DNA
<213> ORGANISM: Vibrio vulnificus
<220> FEATURE:
<221> NAME/KEY: CDS
<222> LOCATION: (756)..(1007)
<220> FEATURE:
<221> NAME/KEY: CDS
<222> LOCATION: (1062)..(2291)

<400> SEQUENCE: 11
```

-continued

```
gtgtacagcc gcctgtggat cccgcatacg cgggaatgac agttgggggc gtggcggcgg     60

tgtgctgagt tttttgttct ttgccgctga acttagctct gctttttctt ttcttatttt    120

tgtcatcctc gcgaacgcgg ggaaccatcc gtcagcaccc gccatcacta actttgaaca    180

caacaatccc agcaacttac gttcactttc cctaaaaaca aaaaagccaa cactctttca    240

agtgttggct tagagactaa agcactaaaa cttagttagt accagtagta ccagtagtac    300

cagtagtgtt gtttgaagaa acaacaactg ctgttgccgc tactgctgca cctgccgcta    360

ctgctgcagt tgttgctgca cccgcgctag ctgcacctgc gccagcacct gctgctgcgc    420

ctgtagaagc agttgtacta gttgctgtag ttgctgttgc agcttcaccc gcagcaaatg    480

cagtagaaga tacacctagt gcaatcaacg ctgctaatgc gatttttttc atgattattc    540

ctttgtatat atacgttttc aaacatcgat gtcggaactt taatagctcc ggtgtttatt    600

ttaggtagaa tttgggcgga atgtaaacaa ttagttgtag ctgcagcgat gtgaatttat    660

ggtttttatc tcattgatag taccgtttgc ttagcaaaaa caattgtgct ctaagccaca    720

atatggataa tatccgccca tgattaatat taata atg aca caa tac tca gtg       773
                                      Met Thr Gln Tyr Ser Val
                                       1               5

tgt cat aaa acg tca gta ctt tgt tgc agc aag cca tta gag cta ttg      821
Cys His Lys Thr Ser Val Leu Cys Cys Ser Lys Pro Leu Glu Leu Leu
            10                  15                  20

cgc agc aaa ttg tcc cag cgc tat gtg gtt ttg cgt gct tac caa agg      869
Arg Ser Lys Leu Ser Gln Arg Tyr Val Val Leu Arg Ala Tyr Gln Arg
        25                  30                  35

gcg gta gcg tgt caa aaa agc cac aaa tat ggg tgg aaa acc aca ctt      917
Ala Val Ala Cys Gln Lys Ser His Lys Tyr Gly Trp Lys Thr Thr Leu
    40                  45                  50

tta acg ggt tct tac att ttc tta cgt tca gtt agc gta gaa tgt tgt      965
Leu Thr Gly Ser Tyr Ile Phe Leu Arg Ser Val Ser Val Glu Cys Cys
 55                  60                  65                  70

gcg aag ctg ctt aaa atc gca gtc agt gtg gga gct agg cta             1007
Ala Lys Leu Leu Lys Ile Ala Val Ser Val Gly Ala Arg Leu
                75                  80

taaagtatag ttaaatgcgg ttaaggaaaa cgcctttaac tatgttgaat acct atg     1064
                                                            Met
                                                             85

ctt tca aaa gcg tta gaa aga aat ggt gtt caa tcg aac ctt tgc tca     1112
Leu Ser Lys Ala Leu Glu Arg Asn Gly Val Gln Ser Asn Leu Cys Ser
                90                  95                  100

ttc aag agt gcc gta aac act ctt aat tta gac gat ttg gct tac atg     1160
Phe Lys Ser Ala Val Asn Thr Leu Asn Leu Asp Asp Leu Ala Tyr Met
            105                 110                 115

gaa cta aaa aca aaa ctt ctg cta gcg atg cta gcg cct gcc ttg ctt     1208
Glu Leu Lys Thr Lys Leu Leu Leu Ala Met Leu Ala Pro Ala Leu Leu
        120                 125                 130

gcc ggt tgt act gta ccc ggc tca cat cta tcc atc gat aat aaa aac     1256
Ala Gly Cys Thr Val Pro Gly Ser His Leu Ser Ile Asp Asn Lys Asn
    135                 140                 145

ctt gtt gaa gtg aac gat agc agc caa gaa agt aac ctt tct gag gtg     1304
Leu Val Glu Val Asn Asp Ser Ser Gln Glu Ser Asn Leu Ser Glu Val
150                 155                 160                 165

gtt aat ctg tat ccg cta aac gct caa tcg gtc acg gaa tac gcc aaa     1352
Val Asn Leu Tyr Pro Leu Asn Ala Gln Ser Val Thr Glu Tyr Ala Lys
                170                 175                 180

gcg cag cat ttt gct tct cgc gca aac cca gaa ctt gat ctg cag atc     1400
Ala Gln His Phe Ala Ser Arg Ala Asn Pro Glu Leu Asp Leu Gln Ile
            185                 190                 195
```

-continued

```
gcc cgt tat gaa tac aaa gtg ggc cct ggc gac att ctt aac gtt acc     1448
Ala Arg Tyr Glu Tyr Lys Val Gly Pro Gly Asp Ile Leu Asn Val Thr
        200                 205                 210

att tgg gat cac cct gag ttg acg att cca gca ggc tct tac cgt agt     1496
Ile Trp Asp His Pro Glu Leu Thr Ile Pro Ala Gly Ser Tyr Arg Ser
    215                 220                 225

gca tcc gaa gta ggt aac tgg gtg cat gca gat ggc acc att ttc tac     1544
Ala Ser Glu Val Gly Asn Trp Val His Ala Asp Gly Thr Ile Phe Tyr
230                 235                 240                 245

cct tac att ggc act gta gaa gtg gca gat aaa aca gtg cgt gag atc     1592
Pro Tyr Ile Gly Thr Val Glu Val Ala Asp Lys Thr Val Arg Glu Ile
                250                 255                 260

cgc gcc gat att gcc aaa cgt ctt gcg aag ttt att gaa agc cca cag     1640
Arg Ala Asp Ile Ala Lys Arg Leu Ala Lys Phe Ile Glu Ser Pro Gln
            265                 270                 275

gtc gat gtc aac gta gcc gcg ttc cgc tct aag aaa gct tac att acc     1688
Val Asp Val Asn Val Ala Ala Phe Arg Ser Lys Lys Ala Tyr Ile Thr
        280                 285                 290

ggt gaa gtt gaa aaa cca ggc caa caa gcc atc acc aat atc cct tta     1736
Gly Glu Val Glu Lys Pro Gly Gln Gln Ala Ile Thr Asn Ile Pro Leu
    295                 300                 305

acc att ctg gat gct gta aac cgt gct ggt ggt cta gcg gaa gat gcc     1784
Thr Ile Leu Asp Ala Val Asn Arg Ala Gly Gly Leu Ala Glu Asp Ala
310                 315                 320                 325

gat tgg cgc aac gtg acg ctt act cgc aat ggt gaa gag caa gcc att     1832
Asp Trp Arg Asn Val Thr Leu Thr Arg Asn Gly Glu Glu Gln Ala Ile
                330                 335                 340

tct ctt tac gcg ctt atg cag cgt ggt gat tta acg caa aac cgt tta     1880
Ser Leu Tyr Ala Leu Met Gln Arg Gly Asp Leu Thr Gln Asn Arg Leu
            345                 350                 355

tta gag ccg ggc gat atc atc cac gtg cca cgc aac gac agc caa aaa     1928
Leu Glu Pro Gly Asp Ile Ile His Val Pro Arg Asn Asp Ser Gln Lys
        360                 365                 370

gtg ttt gta atg ggc gaa gta aaa gat ccc aaa ctg ctt aaa atg gat     1976
Val Phe Val Met Gly Glu Val Lys Asp Pro Lys Leu Leu Lys Met Asp
    375                 380                 385

cgc tct ggc atg agc ctg acg gaa gcc ctc agc agc gtt ggg gga atc     2024
Arg Ser Gly Met Ser Leu Thr Glu Ala Leu Ser Ser Val Gly Gly Ile
390                 395                 400                 405

aac gag ctc tct gcc gat gca acg ggc gtg ttc gtt atc cgt acg tca     2072
Asn Glu Leu Ser Ala Asp Ala Thr Gly Val Phe Val Ile Arg Thr Ser
                410                 415                 420

gac aac aaa tct gaa cgc atg gcg gat atc tac cag ctc aac att aaa     2120
Asp Asn Lys Ser Glu Arg Met Ala Asp Ile Tyr Gln Leu Asn Ile Lys
            425                 430                 435

gat gcc tct gca cta gtg att ggc aca gaa ttc gat cta aaa cca tac     2168
Asp Ala Ser Ala Leu Val Ile Gly Thr Glu Phe Asp Leu Lys Pro Tyr
        440                 445                 450

gat atc gtc tat gtg acc gcc gca cct att act cga tgg aat cgt gtg     2216
Asp Ile Val Tyr Val Thr Ala Ala Pro Ile Thr Arg Trp Asn Arg Val
    455                 460                 465

atc agt cag tta atg cca acg att tat ggc ttt aat gaa cta act gaa     2264
Ile Ser Gln Leu Met Pro Thr Ile Tyr Gly Phe Asn Glu Leu Thr Glu
470                 475                 480                 485

ggt gct cta cgc gtt aaa acg tgg ccg taagatgatt taaaagcggt           2311
Gly Ala Leu Arg Val Lys Thr Trp Pro
                490

cctatggccc ttgggtccta ggggctaatg gattggataa gtctcgtgta agcaaggatg   2371
```

-continued

```
gctgatgagg gttttgggat ttgaaaggct tgaagtatgg aaaaagagtt caagactttc   2431

tgttgatatc gtcaaagccc ttcatcgctg taaaaactat gcattggttg atcagataac   2491

gcgaagtt                                                            2499


<210> SEQ ID NO 12
<211> LENGTH: 494
<212> TYPE: PRT
<213> ORGANISM: Vibrio vulnificus

<400> SEQUENCE: 12

Met Thr Gln Tyr Ser Val Cys His Lys Thr Ser Val Leu Cys Cys Ser
  1               5                  10                  15

Lys Pro Leu Glu Leu Leu Arg Ser Lys Leu Ser Gln Arg Tyr Val Val
             20                  25                  30

Leu Arg Ala Tyr Gln Arg Ala Val Ala Cys Gln Lys Ser His Lys Tyr
         35                  40                  45

Gly Trp Lys Thr Thr Leu Leu Thr Gly Ser Tyr Ile Phe Leu Arg Ser
     50                  55                  60

Val Ser Val Glu Cys Cys Ala Lys Leu Leu Lys Ile Ala Val Ser Val
 65                  70                  75                  80

Gly Ala Arg Leu Met Leu Ser Lys Ala Leu Glu Arg Asn Gly Val Gln
                 85                  90                  95

Ser Asn Leu Cys Ser Phe Lys Ser Ala Val Asn Thr Leu Asn Leu Asp
            100                 105                 110

Asp Leu Ala Tyr Met Glu Leu Lys Thr Lys Leu Leu Leu Ala Met Leu
        115                 120                 125

Ala Pro Ala Leu Leu Ala Gly Cys Thr Val Pro Gly Ser His Leu Ser
    130                 135                 140

Ile Asp Asn Lys Asn Leu Val Glu Val Asn Asp Ser Ser Gln Glu Ser
145                 150                 155                 160

Asn Leu Ser Glu Val Val Asn Leu Tyr Pro Leu Asn Ala Gln Ser Val
                165                 170                 175

Thr Glu Tyr Ala Lys Ala Gln His Phe Ala Ser Arg Ala Asn Pro Glu
            180                 185                 190

Leu Asp Leu Gln Ile Ala Arg Tyr Glu Tyr Lys Val Gly Pro Gly Asp
        195                 200                 205

Ile Leu Asn Val Thr Ile Trp Asp His Pro Glu Leu Thr Ile Pro Ala
    210                 215                 220

Gly Ser Tyr Arg Ser Ala Ser Glu Val Gly Asn Trp Val His Ala Asp
225                 230                 235                 240

Gly Thr Ile Phe Tyr Pro Tyr Ile Gly Thr Val Glu Val Ala Asp Lys
                245                 250                 255

Thr Val Arg Glu Ile Arg Ala Asp Ile Ala Lys Arg Leu Ala Lys Phe
            260                 265                 270

Ile Glu Ser Pro Gln Val Asp Val Asn Val Ala Ala Phe Arg Ser Lys
        275                 280                 285

Lys Ala Tyr Ile Thr Gly Glu Val Glu Lys Pro Gly Gln Gln Ala Ile
    290                 295                 300

Thr Asn Ile Pro Leu Thr Ile Leu Asp Ala Val Asn Arg Ala Gly Gly
305                 310                 315                 320

Leu Ala Glu Asp Ala Asp Trp Arg Asn Val Thr Leu Thr Arg Asn Gly
                325                 330                 335

Glu Glu Gln Ala Ile Ser Leu Tyr Ala Leu Met Gln Arg Gly Asp Leu
            340                 345                 350
```

-continued

Thr Gln Asn Arg Leu Leu Glu Pro Gly Asp Ile Ile His Val Pro Arg
355 360 365

Asn Asp Ser Gln Lys Val Phe Val Met Gly Glu Val Lys Asp Pro Lys
370 375 380

Leu Leu Lys Met Asp Arg Ser Gly Met Ser Leu Thr Glu Ala Leu Ser
385 390 395 400

Ser Val Gly Gly Ile Asn Glu Leu Ser Ala Asp Ala Thr Gly Val Phe
405 410 415

Val Ile Arg Thr Ser Asp Asn Lys Ser Glu Arg Met Ala Asp Ile Tyr
420 425 430

Gln Leu Asn Ile Lys Asp Ala Ser Ala Leu Val Ile Gly Thr Glu Phe
435 440 445

Asp Leu Lys Pro Tyr Asp Ile Val Tyr Val Thr Ala Ala Pro Ile Thr
450 455 460

Arg Trp Asn Arg Val Ile Ser Gln Leu Met Pro Thr Ile Tyr Gly Phe
465 470 475 480

Asn Glu Leu Thr Glu Gly Ala Leu Arg Val Lys Thr Trp Pro
485 490

<210> SEQ ID NO 13
<211> LENGTH: 84
<212> TYPE: PRT
<213> ORGANISM: Vibrio vulnificus

<400> SEQUENCE: 13

Met Thr Gln Tyr Ser Val Cys His Lys Thr Ser Val Leu Cys Cys Ser
1 5 10 15

Lys Pro Leu Glu Leu Leu Arg Ser Lys Leu Ser Gln Arg Tyr Val Val
20 25 30

Leu Arg Ala Tyr Gln Arg Ala Val Ala Cys Gln Lys Ser His Lys Tyr
35 40 45

Gly Trp Lys Thr Thr Leu Leu Thr Gly Ser Tyr Ile Phe Leu Arg Ser
50 55 60

Val Ser Val Glu Cys Cys Ala Lys Leu Leu Lys Ile Ala Val Ser Val
65 70 75 80

Gly Ala Arg Leu

<210> SEQ ID NO 14
<211> LENGTH: 410
<212> TYPE: PRT
<213> ORGANISM: Vibrio vulnificus

<400> SEQUENCE: 14

Met Leu Ser Lys Ala Leu Glu Arg Asn Gly Val Gln Ser Asn Leu Cys
1 5 10 15

Ser Phe Lys Ser Ala Val Asn Thr Leu Asn Leu Asp Asp Leu Ala Tyr
20 25 30

Met Glu Leu Lys Thr Lys Leu Leu Leu Ala Met Leu Ala Pro Ala Leu
35 40 45

Leu Ala Gly Cys Thr Val Pro Gly Ser His Leu Ser Ile Asp Asn Lys
50 55 60

Asn Leu Val Glu Val Asn Asp Ser Ser Gln Glu Ser Asn Leu Ser Glu
65 70 75 80

Val Val Asn Leu Tyr Pro Leu Asn Ala Gln Ser Val Thr Glu Tyr Ala
85 90 95

-continued

```
Lys Ala Gln His Phe Ala Ser Arg Ala Asn Pro Glu Leu Asp Leu Gln
            100                 105                 110

Ile Ala Arg Tyr Glu Tyr Lys Val Gly Pro Gly Asp Ile Leu Asn Val
        115                 120                 125

Thr Ile Trp Asp His Pro Glu Leu Thr Ile Pro Ala Gly Ser Tyr Arg
    130                 135                 140

Ser Ala Ser Glu Val Gly Asn Trp Val His Ala Asp Gly Thr Ile Phe
145                 150                 155                 160

Tyr Pro Tyr Ile Gly Thr Val Glu Val Ala Asp Lys Thr Val Arg Glu
                165                 170                 175

Ile Arg Ala Asp Ile Ala Lys Arg Leu Ala Lys Phe Ile Glu Ser Pro
            180                 185                 190

Gln Val Asp Val Asn Val Ala Ala Phe Arg Ser Lys Lys Ala Tyr Ile
        195                 200                 205

Thr Gly Glu Val Glu Lys Pro Gly Gln Gln Ala Ile Thr Asn Ile Pro
    210                 215                 220

Leu Thr Ile Leu Asp Ala Val Asn Arg Ala Gly Gly Leu Ala Glu Asp
225                 230                 235                 240

Ala Asp Trp Arg Asn Val Thr Leu Thr Arg Asn Gly Glu Glu Gln Ala
                245                 250                 255

Ile Ser Leu Tyr Ala Leu Met Gln Arg Gly Asp Leu Thr Gln Asn Arg
            260                 265                 270

Leu Leu Glu Pro Gly Asp Ile Ile His Val Pro Arg Asn Asp Ser Gln
        275                 280                 285

Lys Val Phe Val Met Gly Glu Val Lys Asp Pro Lys Leu Leu Lys Met
    290                 295                 300

Asp Arg Ser Gly Met Ser Leu Thr Glu Ala Leu Ser Ser Val Gly Gly
305                 310                 315                 320

Ile Asn Glu Leu Ser Ala Asp Ala Thr Gly Val Phe Val Ile Arg Thr
                325                 330                 335

Ser Asp Asn Lys Ser Glu Arg Met Ala Asp Ile Tyr Gln Leu Asn Ile
            340                 345                 350

Lys Asp Ala Ser Ala Leu Val Ile Gly Thr Glu Phe Asp Leu Lys Pro
        355                 360                 365

Tyr Asp Ile Val Tyr Val Thr Ala Ala Pro Ile Thr Arg Trp Asn Arg
    370                 375                 380

Val Ile Ser Gln Leu Met Pro Thr Ile Tyr Gly Phe Asn Glu Leu Thr
385                 390                 395                 400

Glu Gly Ala Leu Arg Val Lys Thr Trp Pro
                405                 410
```